United States Patent
Kondo et al.

(10) Patent No.: US 9,657,324 B1
(45) Date of Patent: May 23, 2017

(54) METHOD FOR TREATING OR PREVENTING MOOD DISORDERS

(75) Inventors: Kazuhiro Kondo, Tokyo (JP); Nobuyuki Kobayashi, Tokyo (JP)

(73) Assignees: VIRUS IKAGAKU KENKYUSHO INC., Toyonaka-shi (JP); JAPAN TOBACCO INC., Tokyo (JP)

(*) Notice: Subject to any disclaimer, the term of this patent is extended or adjusted under 35 U.S.C. 154(b) by 285 days.

(21) Appl. No.: 12/573,636

(22) Filed: Oct. 5, 2009

Related U.S. Application Data

(60) Provisional application No. 61/102,441, filed on Oct. 3, 2008.

(51) Int. Cl.
  *C12Q 1/00* (2006.01)
  *C07K 16/08* (2006.01)
  *G01N 33/68* (2006.01)

(52) U.S. Cl.
  CPC .............. *C12Q 1/00* (2013.01); *C07K 16/085* (2013.01); *G01N 33/6893* (2013.01); *G01N 33/6896* (2013.01)

(58) Field of Classification Search
  CPC ......... G01N 33/6854; G01N 2333/035; G01N 2800/304; G01N 33/6893; G01N 33/6896; G01N 33/54393; G01N 33/56994; G01N 2333/03; G01N 2333/36; G01N 2469/20; G01N 33/54306; G01N 33/54353; C07K 14/005; C07K 2319/70; C12N 2710/16571; C12N 2740/10043; C12N 7/00; C12N 2710/16522; C12N 2710/10343; A01K 2267/0356; A61K 2300/00; A61K 31/33; A61K 31/335; A61K 31/12; A61K 45/06; C07D 493/18
  See application file for complete search history.

(56) References Cited

U.S. PATENT DOCUMENTS

| 2008/0280283 A1 | 11/2008 | Kondo |
| 2010/0281550 A1 | 11/2010 | Kondo et al. |
| 2011/0166106 A1* | 7/2011 | Marschall et al. ............... 514/86 |

FOREIGN PATENT DOCUMENTS

| WO | WO 92/15315 | * | 9/1992 |
| WO | WO 2006/006634 A1 | | 1/2006 |

OTHER PUBLICATIONS

Ljungman et al., Bone Marrow Transplantation, 2007, 39:497-499.*
Asano et al., Journal of Medical Virology, 1990, 32:119-123.*
Pohlmann et al., Clinical Infectious Diseases, 2007, 44:e118-e120.*
Denes et al., Emerging Infectious Diseases, Apr. 2004, 10(4):729-731.*
Kogelnik et al., "Use of valganciclovir in patients with elevated antibody titers against Human Herpesvirus-6 (HHV-6) and Epstein-Barr Virus (EBV) who were experiencing central nervous system dysfunction including long-standing fatigue", Journal of Clinical Virology, Dec. 2006, 37 Suppl.1: S33-38.
Kondo et al., "Association of Human Herpesvirus 6 Infection of the Central Nervous System with Recurrence of Febrile Convulsions", The Journal of Infectious Diseases, 1993, 167, pp. 1197-1200.
Kondo et al., "Identification of Human Herpesvirus 6 Latency-Associated Transcripts", Journal of Virology, Apr. 2002, vol. 76, No. 8, pp. 4145-4151.
Kondo et al., "Latent human herpesvirus 6 infection of human monocytes/macrophages", Journal of General Virology, 1991, 72, pp. 1401-1408.
Kondo et al., "Recognition of a Novel Stage of Betaherpesvirus Latency in Human Herpesvirus 6", Journal of Virology, Feb. 2003, vol. 77, No. 3, pp. 2258-2264.
Kondo, "Human herpesvirus latency and fatigue", 2005, vol. 55, No. 1, pp. 9-17.
Dominguez et al., "Human Herpesvirus 6B Genome Sequence: Coding Content and Comparison with Human Herpesvirus 6A," Journal of Virology, vol. 73, No. 10, pp. 8040-8052, Oct. 1999, XP002609006.
Extended European Search Report, dated Dec. 21, 2010, for European Application No. 08833887.6.
International Search Report, dated Oct. 28, 2008, for International Application No. PCT/JP2008/067300, with English translation.
Kobayashi et al., "Hito Herpesvirus (HHV)-6 Senpuku Kansen Tokuiteki Tanpaku ni yoru Utsu Shojo no Hassho Kijo," Dai 55 Kai The Japanese Society of Virology Gakujutsu Shukai Program, Shorokushu p. 120, Oct. 1, 2007, with an English translation.
Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, Heisei 17 Nendo Sokatsu•Buntan Kenkyu Hokokusho. pp. 19-23, Mar. 2006, with a partial English translation.

(Continued)

*Primary Examiner* — Nicole Kinsey White
(74) *Attorney, Agent, or Firm* — Birch, Stewart, Kolasch & Birch, LLP

(57) ABSTRACT

The present invention is directed to methods of treating a subject, wherein a biological sample taken from the subject comprises an antibody against a small protein encoded by an intermediate stage transcript of HHV-6 (SITH-1), and the antibody against SITH-1 being present in an amount sufficient to be detected in the biological sample which is at least diluted 10-fold or more by an immunological detection method. Such treatment methods are used for the following: a) treating or preventing mood disorders; b) suppressing an elevation of the level of SITH-1 within cells in the subject's brain, reducing the number of cells in the brain that carry the protein SITH-1, and/or reducing the total amount of SITH-1 in the brain; c) suppressing an elevation of the level of a calcium modulating cyclophilin ligand (CAML) protein within cells in the subject's brain; or d) suppressing an elevation of the level of calcium ions within cells in the subject's brain. Methods of the present invention can involve administering a human herpesvirus 6 suppressor to a subject.

15 Claims, 9 Drawing Sheets

(56) References Cited

OTHER PUBLICATIONS

Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, Heisei 18 Nendo Sokatsu•Buntan Kenkyu Hokokusho, pp. 13-18, Mar. 2007, with a partial English translation.

Kondo et al., "Shinkei Shikkan Oyobi Shokaki Shikkan no Kiin Virus no Kaimei," Tokutei Shikkan no Biseibutsugakuteki Gen'in Kyumei ni Kansuru Kenkyu, Heisei 19 Nendo Sokatsu•Buntan Kenkyu Hokokusho, pp. 17-23, Mar. 2008, with a partial English translation.

Kondo et al., "Identification of a novel HHV-6 latent-protein associated with CFS and mood disorders", Neuroscience Research, vol. 68S, p. e51, XP002609007, 2010.

Kondo, "Hito Herpesvirus 6 (HHV-6) to CFS," Prog. Med., vol. 25, pp. 1315-1319, 2005, with a partial English translation.

Kondo, "Virus no Senpuku Kansen Tanpakushitsu to Hiro," Molecular Medicine, vol. 41, No. 10, pp. 1216-1221, 2004, with a partial English translation.

Patnaik et al., "Prevalence of IgM Antibodies to Human Herpesvirus 6 Early Antigen (p41/38) in Patients with Chronic Fatigue Syndrome", The Journal of Infectious Diseases, vol. 172, No. 5, pp. 1364-1367, XP002609186, Nov. 1995.

Reeves et al., "Human Herpesviruses 6 and 7 in Chronic Fatigue Syndrome: A Case-Control Study", Clinical Infectious Diseases, vol. 31, No. 1, pp. 48-52, XP-002609184, Jul. 2000.

Wallace et al., "Human Herpesviruses in Chronic Fatigue Syndrome", Clinical and Diagnostic Laboratory Immunology, vol. 6, No. 2, pp. 216-223, XP002609185, Mar. 1999.

XP002609118, Amino Acid Sequence of Gene Product U91 from Human Herpesvirus 6B Accession No. Q9QJ14 in Swiss-Protein Database at NCBI.

Kobayashi et al., 6th International Conference on HHV-6, 7, Baltimore, Maryland, USA, Jun. 22, 2008.

Kobayashi et al., International Conference on Fatigue Science 2008, Sep. 4, 2008.

Kondo, Japan Herpes Virus Infections Forum, JHIF, Aug. 23, 2008.

Kondo, K., The 55th Autumn Meeting of Japan Society of Allergology, Nov. 2, 2007, with English partial translation.

* cited by examiner

METHOD FOR TREATING OR PREVENTING MOOD DISORDERS

CROSS-REFERENCE

This Nonprovisional application claims priority under 35 U.S.C. §119(e) to U.S. Provisional Application No. 61/102,441 filed on Oct. 3, 2008, the entire contents of which are hereby incorporated by reference.

TECHNICAL FIELD

The present invention relates to a method for treating or preventing mood disorders.

BACKGROUND OF THE INVENTION

1) Mood Disorders

Mood disorders refers to states in which mood (emotional) disturbances that persist over a certain period of time cause pain to be felt or present with some trouble in everyday life; they are symptoms found in mental disorders such as depression and manic-depressive illness. Depression that presents with only symptoms of depression and manic-depressive illness in which episodes of mania alternate with episodes of depression are two most typical examples. While various factors have been proposed as causes of mood disorders, most remain unclear about details.

2) Herpes Virus

Viruses of the family Herpesviridae are such that a core protein is surrounded by double-stranded DNA with molecular masses of 80-150×$10^6$ Daltons that is enclosed in an icosahedral capsid with a diameter of about 100 nm that consists of 162 capsomers to form a nucleocapsid which is surrounded by an envelope to have an overall size of ca. 150-200 nm. Herpes viruses have been found in almost all mammals and amphibians and, in particular, viruses of the family Herpesviridae that have host specificity for humans are named human herpesviruses (HHVs). HHVs are classified into subfamilies Alpha herpesvirinae (e.g., herpes simplex virus and varicella zoster herpes virus), Beta herpesvirinae (e.g., cytomegalovirus), and Gamma herpesvirinae (e.g., EB virus).

These herpes viruses can pass through four stages of their life cycle, cell infection, latent infection, proliferation, and reactivation. "Latent infection" refers to such a state of infection that a virus that has infected a host cell will not produce infectious virions within the host cell but continues to survive. Even in this phase of latent infection, the virus genes and the gene products that help them to exist are retained within the host cell. Herpes viruses that exhibit latent infection are known to resume viral replication and produce large amounts of virions owing to certain causes on the side of the host (e.g., aging and somatic complaints (including fatigue)). This state is called "reactivation." In addition, the "proliferation" of a virus refers collectively to such stages that the virus increases the numbers of its genes and virions.

In short, herpes viruses have such a unique character that they continue to infect the host latently as long as it has nothing abnormal but that once a somatic disturbance occurs in the host and the virus detects that the host is in danger, it is reactivated to seek another, healthy host.

To study the biology of such viruses of the family Herpesviridae, understanding their latent infection and reactivation is essential. However, among the many herpes viruses, it is only EB virus which belongs to the subfamily Gamma herpesvirinae that has been studied to yield many findings about latent infection and much remains unclear about other viruses.

In particular, concerning factors that may be involved in the latent infection of Beta herpesvirinae, there has been obtained no information other than from the findings previously published by the present inventors. For example, Non-Patent Document 1 discloses latent infection of HHV-6 in macrophages in peripheral blood that have differentiated to a fairly high extent and identifies the sites in a host at which it is latently infected with HHV-6. Non-Patent Document 2 describes very frequent invasion of HHV-6 into the brain upon primary infection to cause persistent infection and latent infection. Non-Patent Document 3 discloses genes (latent infection genes) that are expressed during latent infection of HHV-6 and it suggests that those genes play the role of regulating the latent infection and reactivation of the virus.

Non-Patent Document 4 shows that the state of latent infection with HHV-6 involves an intermediate stage which is comparatively stable and allows for active gene expression, with the result that a latent infection gene and a protein encoded by this gene (the latent infection gene protein) are expressed abundantly. What is more, Non-Patent Document 5 shows that patients with chronic fatigue syndrome had in their sera antibodies to latent infection gene proteins the expression of which is enhanced at the intermediate stage.

The chronic fatigue syndrome (CFS) as used herein is a disease that causes severe fatigue to be felt for at least six months with no distinct reason and the diagnostic criteria for CFS are as follows: 1. The state where the patient has to miss several days of work or school a month on account of the disabling fatigue that is felt persists or relapses for at least six months; and 2. No other diseases are suspected. The symptoms of CFS include: (1) slight fever or chills; (2) sore throat; (3) swollen lymph nodes; (4) weakness of unknown cause; (5) muscle pain; (6) general feeling of malaise; (7) headache; (8) joint pain; (9) psychoneurotic symptoms; (10) sleep disorders; (11) sudden onset; the diagnosis is confirmed if at least eight of these symptoms are recognized (Non-Patent Document 5). It should be noted here that CFS is categorized as a different disease from mood disorders and a diagnosis of CFS is rejected if bipolar I disorders (manic-depressive illness and bipolar depression) are suspected. Finally, Non-Patent Document 6 describes a case in which patients who were presenting with encephalitis/encephalopathy-like symptoms and long-standing fatigue symptoms, presumably due to the infection with HHV-6 or Epstein-Barr virus (EBV), were administered with the anti-herpes viral agent valganciclovir, with the result that 75% of the patients had their symptoms improved.

Non-Patent Document 1: Kondo, K., et al. Latent human herpesvirus 6 infection of human monocytes/macrophages (J Gen Virol 72:1401-1408, 1991)

Non-Patent Document 2: Kondo, K., et al. Association of human herpesvirus 6 infection of the central nervous system with recurrence of febrile convulsions. (J Infect Dis 167:1197-1200, 1993)

Non-Patent Document 3: Kondo, K., et al. Identification of human herpesvirus 6 latency-associated transcripts. (J Virol. 76: 4145-4151, 2002)

Non-Patent Document 4: Kondo, K., et al. Recognition of a Novel Stage of Beta-Herpesvirus Latency in Human Herpesvirus 6. (J Virol. 77: 2258-2264, 2003)

Non-Patent Document 5: Kondo, K.; "Herupesu uirus kansen to hirou (Infection with Herpes Viruses and Fatigue)" in Virus, Vol. 55, No. 1, pp. 9-17, 2005

Non-Patent Document 6: Montoya, J. G., et al. (J Cli Virol. 2006 December; 37 Suppl:S33-8).

SUMMARY OF THE INVENTION

The present invention intends to cover the following individual, whose biological sample is diluted 10-fold or more and yet enables an antibody against the small protein encoded by the intermediate stage transcript of HHV-6 (SITH-1) to be detected by an immunological detection method using an immunological antigen-antibody technique, and aims to achieve any one of the following purposes:

a) treating or preventing mood disorders;

b) suppressing an elevation of the level of SITH-1 within cells in the brain of the individual, reducing the number of cells in the brain that carry the protein SITH-1, and/or reducing the total amount of SITH-1 in the brain;

c) suppressing an elevation of the level of a calcium modulating cyclophilin ligand (CAML) protein within cells in the brain of the individual; or d) suppressing an elevation of the level of calcium ions within cells in the brain of the individual.

The method of the present invention comprises administering a human herpesvirus 6 suppressor to the individual.

Certain aspects of the present invention are directed to methods of treating a subject with a mood disorder or a subject susceptible to a mood disorder that comprise administering to the subject a therapeutically effective dose of at least one human herpesvirus 6 (HHV-6) suppressor, wherein a biological sample taken from the subject comprises an antibody against a small protein encoded by an intermediate stage transcript of HHV-6 (SITH-1), the antibody against SITH-1 being present in an amount sufficient to be detected in the biological sample which is at least diluted 10-fold or more by an immunological detection method.

Some aspects of the present invention are directed to methods of treating a subject that comprise administering to the subject a therapeutically effective dose of at least one human herpesvirus 6 (HHV-6) suppressor, wherein a biological sample taken from the subject comprises an antibody against a small protein encoded by an intermediate stage transcript of HHV-6 (SITH-1), the antibody against SITH-1 being present in an amount sufficient to be detected in the biological sample which is at least diluted 10-fold or more by an immunological detection method, and wherein the dose of the HHV-6 suppressor administered is sufficient to suppress an elevation of the level of SITH-1 protein within cells of the subject's brain, reduce the number of cells carrying SITH-1 protein within the subject's brain, and/or reduce the total amount of SITH-1 protein in the subject's brain. In some aspects of the present invention, the cells in the subject's brain affected by the inventive methods are glial cells.

Certain aspects of the present invention are directed to methods of treating a subject that comprise administering to the subject a therapeutically effective dose of at least one human herpesvirus 6 (HHV-6) suppressor, wherein a biological sample taken from the subject comprises an antibody against a small protein encoded by an intermediate stage transcript of HHV-6 (SITH-1), the antibody against SITH-1 being present in an amount sufficient to be detected in the biological sample which is at least diluted 10-fold or more by an immunological detection method, and wherein the dose of the HHV-6 suppressor administered is sufficient to suppress an elevation of the level of a calcium modulating cyclophilin ligand (CAML) protein within cells of the subject's brain. In certain aspects of the present invention, the cells in the subject's brain affected by the inventive methods are glial cells.

Some aspects of the present invention are directed to methods of treating a subject that comprise administering to the subject a therapeutically effective dose of at least one human herpesvirus 6 (HHV-6) suppressor, wherein a biological sample taken from the subject comprises an antibody against a small protein encoded by an intermediate stage transcript of HHV-6 (SITH-1), the antibody against SITH-1 being present in an amount sufficient to be detected in the biological sample which is at least diluted 10-fold or more by an immunological detection method, and wherein the dose of the HHV-6 suppressor administered is sufficient to suppress an elevation of the level of calcium ions within cells of the subject's brain. In some aspects of the present invention, the cells in the subject's brain affected by the inventive methods are glial cells.

Certain aspects of the present invention are directed to methods of treating a subject diagnosed with a mood disorder or identified as being at high risk for developing a mood disorder.

In some aspects of the present invention an HHV-6 suppressor administered to a subject may be an anti-human herpesvirus 6 drug (anti-HHV-6 drug) or a virus reactivation suppressor. In certain aspects of the present invention, a subject may be administered an anti-HHV-6 drug that may be selected from the group consisting of acyclovir, ganciclovir, valganciclovir, foscarnet, famciclovir, and idoxuridine (IDU). In some embodiments of the present invention, a virus reactivation suppressor may be administered to a subject that may be selected from the group consisting of D-ribose, vitamin C, and an active hexose correlated compound (AHCC).

The biological sample used in some aspects of the present invention may be blood, serum, cerebrospinal fluid, saliva, sweat, lymph, or breast milk.

In some aspects of the present invention the SITH-1 protein may be encoded by: (1) a nucleic acid coding for a protein comprising the amino acid sequence of SEQ ID NO: 1; (2) a nucleic acid coding for a protein comprising an amino acid sequence that is at least 80%, at least 85%, at least 90%, at least 95%, or at least 98% identical to the amino acid sequence of SEQ ID NO: 1, wherein the protein has a biological activity of a protein having SEQ ID NO: 1; (3) a nucleic acid comprising the nucleotide sequence of SEQ ID NO: 2; or (4) a nucleic acid which hybridizes with a nucleic acid comprising a nucleotide sequence complementary to the nucleotide sequence of SEQ ID NO: 2 under stringent hybridizing conditions and coding for a protein having a biological activity of a protein having SEQ ID NO: 1.

Some aspects of the present invention are directed to methods of treating or preventing mood disorders that comprise administering a human herpesvirus 6 suppressor to a subject, wherein a biological sample taken from the subject contains more of SITH-1 protein encoded by an intermediate stage transcript of HHV-6 and/or an antibody against SITH-1 protein than that of a healthy subject.

Certain aspects of the present invention are directed to methods of treating or preventing mood disorders that comprise administering to a subject with a mood disorder or a subject likely to suffer from mood disorder (a) a human herpesvirus 6 suppressor, or (b) an agent that suppresses human herpesvirus 6 infection, proliferation, latent infection and/or reactivation.

In some aspects of the present invention, a HHV-6 suppressor may be administered to a subject after a biological sample has been taken from the subject and the SITH-1 protein or antibody to the SITH-1 protein has been detected.

Some aspects of the present invention are directed to methods of treating a subject diagnosed with a mood disorder or a subject susceptible to a mood disorder. Certain aspects of the present invention are directed to method of treating a subject diagnosed with chronic fatigue syndrome and a mental disorder.

Certain aspects of the present invention are directed to methods of treating a subject that comprise (1) collecting a biological sample from the subject, wherein the biological sample comprises an antibody against a small protein encoded by an intermediate stage transcript of HHV-6 (SITH-1), (2) diluting the biological sample at least 10-fold, (3) contacting the diluted biological sample with a detector for the SITH-1 antibody, (4) permitting SITH-1 antibody-detector complexes to form between the detector and SITH-1 antibody present in the biological sample, (5) detecting the SITH-1 antibody-detector complexes by an immunological detection method, and (6) administering to the subject a therapeutically effective dose of at least one HHV-6 suppressor, when there are sufficient SITH-1 antibody-detector complexes formed that they are capable of being detected. In some aspects of the present invention, the detector may comprise an antibody to SITH-1 antibody.

Some aspects of the present invention are directed to methods of diagnosing a subject as having a human herpesvirus 6 infection that comprise (1) collecting a biological sample from the subject, (2) diluting the biological sample at least 10-fold, (3) contacting the diluted biological sample with a detector for an antibody against a small protein encoded by an intermediate stage transcript of HHV-6 (SITH-1), (4) permitting SITH-1 antibody-detector complexes to form between the detector and any SITH-1 antibody present in the biological sample, (5) detecting the SITH-1 antibody-detector complexes by an immunological detection method. In some aspects of the present invention, the detector may comprise an antibody to SITH-1 antibody.

BRIEF DESCRIPTION OF THE DRAWINGS

FIG. 5 is a diagram showing that the protein SITH-1 increased the amount of CAML in an astrocyte-like glial cell line.

DETAILED DESCRIPTION OF THE INVENTION

Figure 1:
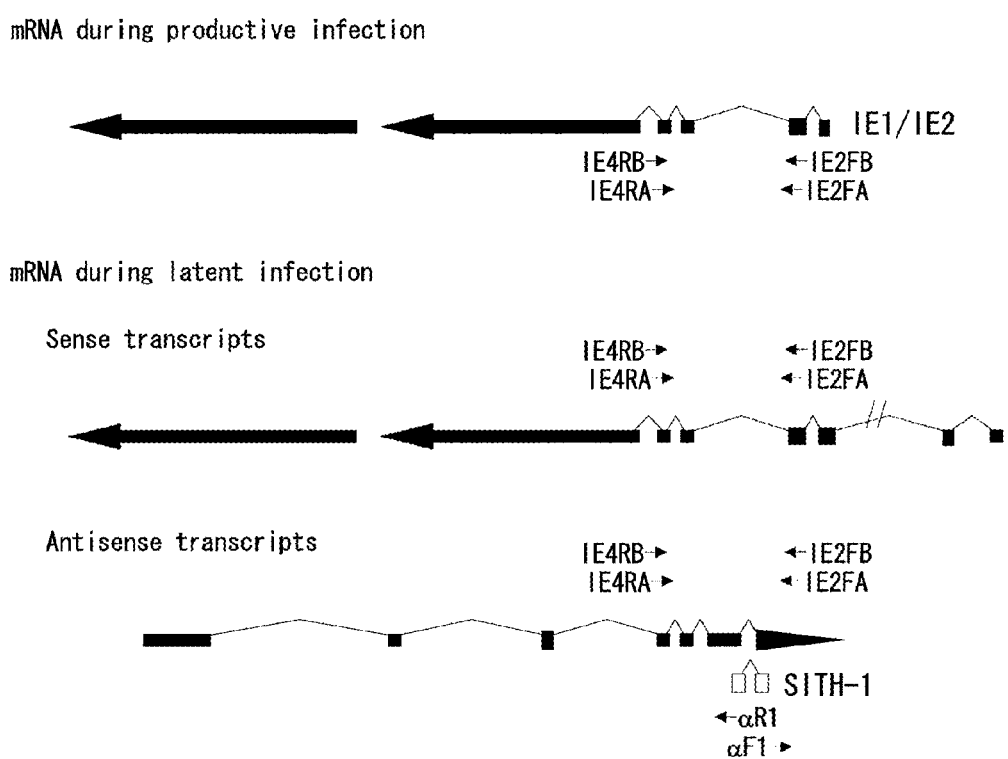
FIG. 1 is a diagram showing schematically the structure of a latent infection specific gene product and the positions of analytical primers.

The present inventors made intensive studies with a view to unraveling the mechanism of mood disorders and establishing a method for treating and/or preventing such disorders and, as a result, they conceived of the present invention.

The contents of a commonly assigned, pending earlier application (International Application PCT/JP2008/67300 submitted on Sep. 25, 2008 claiming the priority based on Japanese Patent Application 2007-250461 filed on Sep. 27, 2007) is incorporated herein by reference in its entirety.

Description Based on the Contents of International Application PCT/JP2008/67300

A novel gene to be expressed at the intermediate stage where genes specific for the latent infection with HHV-6 will be expressed actively and a novel protein encoded by that gene, or a small protein encoded by the intermediate stage transcript of HHV-6 (SITH-1), were identified. The result was: (i) the protein SITH-1 had the capacity to elevate the intracellular calcium level; and (ii) antibodies to the protein SITH-1 were detected significantly in patients with mood disorder whereas they were hardly detected in healthy persons.

Stated in detail, the present inventors speculated that infection with HHV-6 among the various kinds of human herpes viruses was most probably a cause of mental disorders, particularly ones accompanied by mood disorders. The reasons include: (i) among the symptoms of chronic fatigue syndrome (CFS) for which HHV-6 has heretofore been held as one cause, depressive symptoms and others that are often found in mental disorders are recognized; (ii) HHV-6 causes latent infection in the brain; and (iii) antibodies reactive with the heretofore identified HHV-6 latent infection specific gene proteins, as well as antibodies reactive with unknown proteins that were expressed in cells latently infected with HHV-6 but which were yet to be identified for genes or for themselves were detected at high frequencies.

And in light of the fact that the primary sites in the brain which are latently infected with HHV-6 include the frontal lobe and hippocampal region that govern the human thought and emotions, as well as the fact that the viruses that cause latent infection in the brain are just a few including HHV-6, the present inventors speculated the relation between HHV-6 and mental disorders. Further, HHV-6 is known to cause latent infection in glial cells such as astrocytes that play important roles in the metabolism of serotonin and other substances within the brain that are associated with depression.

Thus, the present inventors speculated that patients with CFS might include considerable cases who present with certain mental symptoms on account of the latent infection of the brain with HHV-6. In particular, the present inventors speculated the relation between HHV-6 and mood disorders such as depression and manic-depressive illness.

Mood disorders are symptoms found in mental disorders such as depression and manic-depressive illness, and two most typical examples are depression that presents with only symptoms of depression and manic-depressive illness in which episodes of mania alternate with episodes of depression. While various possible causes have been proposed, including stress, genetic aberrations, and infection, no single factor has yet been established. The incidence of mood disorders is increasing these days and since this is becoming a big social problem, it is desirable that to the etiology and pathology of each mood disorder are unraveled and methods for diagnosing and treating it are developed as soon as possible. A problem worth particular mention here is that the diagnoses of mood disorders are liable to be only qualitative and involve difficulty in achieving objectivity.

(1) Protein SITH-1 and the Associated Nucleic Acid
(1-1) Structure

The small protein encoded by the intermediate stage transcript of HHV-6 (SITH-1) is a factor that is involved in the latent infection with the herpes virus and, stated in greater detail, it is a protein that is expressed specifically during latent infection with the herpes virus. The phrase reading "expressed specifically during latent infection with the herpes virus" means that a gene or a gene product as derived from the herpes virus is expressed specifically in a virally infected host while it is latently infected (but not productively infected) with the herpes virus.

The protein SITH-1 and the associated nucleic acid are exemplified by a protein comprising the amino acid sequence depicted in SEQ ID NO:1, and a nucleic acid coding for this protein.

As will be described later in the Reference Example, the protein SITH-1 comprising the amino acid sequence depicted in SEQ ID NO:1 has been isolated and identified as a protein that is specifically expressed during the latent infection with human herpesvirus-6 (HHV-6). The protein SITH-1 is a protein with a molecular mass of ca. 17.5 kDa that has the amino acid sequence depicted in SEQ ID NO:1 and consists of 159 amino acids.

The protein SITH-1 is encoded by the nucleic acid of the SITH-1 gene. As depicted in SEQ ID NO:3, the cDNA of the SITH-1 gene has a size of 1795 base pairs (ca. 1.79 kbp) and the $954^{th}$ to $956^{th}$ nucleotide sequence represents a start codon (Kozak ATG) whereas the $1431^{st}$ to $1433^{rd}$ nucleotide sequence represents a stop codon (TAA). Hence, the nucleic acid associated with SITH-1 has an open reading frame (ORF) that consists of the $954^{th}$ to $1430^{th}$ nucleotide sequence of those depicted in SEQ ID NO:3, with the ORF having a size of 477 base pairs (ca. 0.48 kbp). The nucleotide sequence that represents the ORF region of the cDNA of SITH-1 is depicted in SEQ ID NO:2. Note that the nucleotide sequence as depicted in SEQ ID NO:2 includes the three nucleotides of the stop codon.

(1-2) Functions

As will be described later, the SITH-1 nucleic acid was expressed at all times in the cytoplasm of cells latently infected with HHV-6, but not in productively infected cells. The nucleic acid that codes for the protein SITH-1 is encoded by DNA forming a complementary strand to the previously reported HHV-6 latent infection specific gene (H6LT) and its expression is enhanced at the intermediate stage of latent infection with HHV-6.

From these facts, the protein SITH-1 is considered to be a protein that is expressed specifically during latent infection with HHV-6 and it has been found to be clearly different from the heretofore-identified proteins that are involved in the latent infection with HHV-6.

The protein SITH-1 binds to the host protein CAML (calcium-modulating cyclophilin ligand, Accession #; U18242) to elevate the calcium level in glial cells. CAML is a protein that occurs abundantly within the brain and lymphocytes in the host's living body, and is known to elevate the calcium level in cells. When the protein SITH-1 is expressed in cells, the number of CAML in cells is increased, and as a result, the intracellular calcium level is elevated. Such elevation in the intracellular calcium level due to the expression of the protein SITH-1 is considered to induce activation of general signal transmission within the latently infected cell, thereby contributing to efficient reactivation of HHV-6. Also it has been found that protein SITH-1 up-regulates 5100 beta in protein level and mRNA level.

By the term "glial cells" as used herein are meant all kinds of glial cells including mature and precursor forms of glial cells in the central nervous system, as exemplified by astrocytes, oligodendrocytes, microglias, and ependymal cells. Other types that may be embraced are satellite cells, Schwann cells and terminal gliocytes in the peripheral nervous system.

HHV-6 is known to cause latent infection of glial cells in the brain and it is believed that the calcium level in glial cells rises if HHV-6, either during latent infection or at its intermediate stage characterized by high activity, causes SITH-1 to be expressed. Elevation of the intracellular calcium level within brain cells is considered to be closely related to mood disorders and other mental disorders (RIKEN Annual Report 2003).

In fact, as will be shown in the Reference Example, expressing the protein SITH-1 in mouse glial cells turned out to induce both symptoms similar to those of mood disorders as mental disorders and increased sensitivity. This strongly suggests the possibility that HHV-6 latently infecting glial cells in the brain can trigger a mental disorder via the protein SITH-1.

As described above, the protein SITH-1 has the capacity to retain the activity for binding to the host protein CAML and elevate the intracellular calcium level.

It has also been found that a mental disorder can be induced by causing the protein SITH-1 to be expressed in glial cells within the brain where the strongest expression of this protein is likely to occur. Thus, the protein SITH-1 is considered to have the capacity to cause a mental disorder in the host by being expressed during latent infection with the herpes virus or at the early stage of its reactivation.

(1-3) Methods of Acquiring the Nucleic Acid and the Protein

The methods of acquiring (or producing) the SITH-1 nucleic acid and the protein SITH-1 are not particularly limited and they can be acquired by known methods.

(2) Antibody to SITH-1

The antibody to SITH-1 is obtained as a polyclonal or monoclonal antibody by known methods using the protein SITH-1 or its variant or a partial peptide thereof as an antigen. Known methods include those that are described in documents such as Harlow et al., "Antibodies: A laboratory manual (Cold Spring Harbor Laboratory, New York (1988) and Iwasaki et al., "Tankurohn koutai haiburidoma to ELISA (Monoclonal Antibody Hybridomas and ELISA)", Kodansha (1991)). The thus obtained antibody may be utilized in detecting and assaying the protein SITH-1.

The term "antibody" means immunoglobulins (IgA, IgD, IgE, IgG IgM and their Fab fragments, F(ab')$_2$ fragments, and Fc fragments); examples include, but are not limited to, polyclonal antibodies, monoclonal antibodies, single-chain antibodies, anti-idiotype antibodies, and humanized antibodies.

The term "antibody that recognizes the protein SITH-1" is intended to encompass complete molecules and antibody fragments that are capable of binding to the protein SITH-1 specifically (e.g., Fab and F(ab')$_2$ fragments). The Fab and F(ab')$_2$ fragments, as well as other fragments of the SITH-1 antibody may be used in accordance with the methods disclosed herein or any known methods. These fragments are typically produced by proteolysis using such enzymes as papain (to generate the Fab fragment) or pepsin (to generate the F(ab')$_2$ fragment).

When detecting elevated levels of the protein SITH-1 using in vivo imaging for the purpose of diagnosis on humans, it can be preferable to use "humanized" chimeric monoclonal antibodies. These antibodies can be generated using genetic constructs derived from hybridoma cells that generate the above-mentioned monoclonal antibodies. Methods for generating chimeric antibodies are known in the art of interest.

(3) Utility of the SITH-1 Nucleic Acid and the Protein SITH-1

The SITH-1 nucleic acid and the protein SITH-1 have been found to be related to patients with mental disorders. Stated in greater detail, as will be shown in the Reference Example later, the anti-SITH-1 antibody was detected in about 50% of patient groups suffering from mood disorder or other mental disorders but it was hardly detectable in healthy persons (the frequency of its detection in healthy persons was less than about 2%).

Thus, the present inventors have discovered on their own that antibodies specific to the protein SITH-1 are found significantly only in patients with mood disorders and other mental disorders but are hardly detectable in healthy persons. Note that the "mental disorders" as used herein is intended to mean such a state that the daily life or social life undergoes considerable limit on account of disorders in mental functions such as consciousness, intelligence, memory, emotions, thought, and behavior. The "mood disorders" is intended to mean such a state that because of persistent mood or emotional changes, abnormally depressive or elated feelings are experienced to bring disturbances into daily life functioning or social life functioning.

The protein SITH-1 has such a nature that it is actively produced at the intermediate stage where latent infection is induced toward reactivation. It is believed that in response to a stress, reactivation of herpes viruses (say, HHV-6) is induced, whereby the protein SITH-1 is produced. Persons who have the antibody to the protein SITH-1, accounting for about 50% of patients with mental disorders, are considered to have that protein expressed abundantly for a prolonged period in glial cells in the brain which are latently infected with HHV-6 because of stress or a certain genetic factor. As a result, the elevation of the calcium level in glial cells continues for a prolonged period and serotonin metabolism and other important functions of glial cells are impaired, whereby a mental disorder would manifest itself. In addition, concerning the mental disorders in patients with chronic fatigue syndrome (CFS), the reason that the frequency of those patients who carry the antibody to the protein SITH-1 is high (ca. 40%) would be that the patients with CFS are often latently infected with greater numbers of HHV-6 than healthy persons are, thus having a greater likelihood for the production of the protein SITH-1. The fact that the patients with CFS are latently infected with greater numbers of HHV-6 than healthy persons are is also supported by the result of the reaction between the previously reported latent infection specific gene product and the antibody in CFS patients (see Non-Patent Document 5).

There is provided a method for determining whether an antibody that recognizes the protein SITH-1 is present in an organism under test.

An assay for the antibody enables detection by, for example, the reaction for binding to a protein recognized by the antibody or a partial fragment thereof. Thus, in this method of determination, a protein recognized by the antibody or a partial fragment thereof is preferably used to determine for the presence of the antibody of interest in an immunological manner (i.e., using an antigen-antibody reaction). Note that the "partial fragment" preferably contains at least an epitope-carrying peptide.

To give an example of this method of determination, an insoluble carrier on which the protein according to the present invention or a partial fragment thereof is immobilized is brought into contact with a biological sample taken from an organism under test and washed, and then the antibodies specifically bound to the protein or its partial fragment on the insoluble carrier are detected. Since the antibodies specifically bound to the protein or its partial fragment on the insoluble carrier are typically derived from the organism under test, they can be easily detected with a secondary antibody, or an antibody specific to the antibodies in the organism under test. In this case, a dye, an enzyme or a radioactive or fluorescent label may be incorporated in the secondary antibody so as to enhance and thereby further facilitate the intended detection.

Thus, antibody assays to be used in the method of determination under consideration include assay techniques that make use of traditional immunohistological approaches such as a (indirect) fluorescent antibody technique, a dot blot assay, a western blotting technique, enzyme-linked immunosorbent assay techniques (including ELISA and a sandwich ELISA technique), a radioimmunoassay technique (RIA), and an immunodiffusion assay technique. These assays often use molecules such as avidin and biotin for the purposes of molecular immobilization and detection, and techniques for preparing these reagents and methods of using them are available as technologies known to skilled artisans. Note that the result of the method of determination under consideration is an immunohistological stain of tissue sections for pathological testing.

Note also that the method of determination under consideration is preferably performed using a biological sample isolated from the organism under test. The term "biological sample isolated" may cover any sample that contains fluid, cells, tissues or disrupted pieces thereof as taken from the organism under test; the applicable sample is not particularly limited but in view of the fact that herpes viruses latently infect macrophages in peripheral blood, it is particularly preferable to use peripheral blood taken from the organism under test. In this case, the organism under test benefits from a low degree of invasion.

The amount of antibodies present in the biological sample can be readily calculated by making comparison with the amount present in a standard preparation (e.g., a standard sample from a healthy person or one from a typical patient with mental disorder), typically using a linear regression computer algorithm. While various assay techniques are available for antibody detection, an example for ELISA is described in Iacobelli et al., Breast Cancer Research and Treatment 11: 19-30 (1988).

Suitable enzyme labels may be exemplified by those derived from a class of oxidases which catalyze the generation of hydrogen peroxide through reaction with the substrate. Glucose oxidase is particularly preferred since it has satisfactory stability and its substrate (glucose) is easily available. The activity of the oxidase label can be assayed by measuring the concentration of hydrogen peroxide as formed by the enzyme-labeled antibody/substrate reaction. In addition to enzymes, other suitable labels include radioisotopes (e.g., iodine ($^{125}$I and $^{121}$I), carbon ($^{14}$C), sulfur ($^{35}$S), tritium ($^{3}$H), indium ($^{112}$In), and technetium ($^{99m}$Tc), as well as fluorescent labels (e.g., fluorescein and rhodamin) and biotin.

The level of antibodies (against the protein SITH-1) that are present in biological samples obtained from the organism under test can also be detected by methods other than the above-described immunoassay technique, for example, by in vivo image analysis. In short, in view of the fact that the antibody against the protein according to the present invention is also a protein, an antibody that recognizes this antibody may be used for in vivo detection by image analysis of the level of antibodies (against the protein SITH-1) that are present in biological samples obtained from the organism under test.

Antibody labels or markers for the in vivo image analysis of antibodies include those that can be detected by X-ray imaging, NMR, or ESR. For X-ray imaging, suitable labels include radioisotopes such as barium or cesium that emit detectable radiation but which are obviously harmless to the sample under test. Suitable markers for NMR and ESR include those which can be used to label a nutrient for culturing an associated hybridoma to produce a corresponding antibody, whereby the label is incorporated in the antibody produced; an example of such label is deuterium having a detectable characteristic spin.

An antibody or a fragment thereof that is specific for the antibody against the protein SITH-1 that is labeled with a suitable, detectable portion for image analysis, such as a radioisotope (e.g., $^{131}$I, $^{111}$In, or $^{99m}$Tc), a radio-opaque substrate or a substance detectable by nuclear magnetic resonance is introduced (e.g., parenterally, subcutaneously, or intravenously) into a mammal to be tested for a disorder. It will be understood in the art of interest that the quantity of the portion for image analysis that is considered necessary for generating a diagnostic image is determined by the size of the sample under test and the image analysis system to be used. In the case where that portion is part of a radioisotope, the quantity of radioactivity to be injected into a human sample is typically in the range of from about 5 to about 20 mCi of $^{99m}$Tc.

Examples of suitable enzyme labels include malate dehydrogenase, *Staphylococcus* nuclease, yeast alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotope labels include $^{3}$H, $^{111}$In, $^{125}$I, $^{131}$I, $^{32}$P, $^{35}$S, $^{14}$C, $^{51}$Cr, $^{57}$Co, $^{58}$Co, $^{59}$Fe, $^{75}$Se, $^{152}$Eu, $^{90}$Y, $^{67}$Cu, $^{211}$At, $^{212}$Pb, $^{47}$Sc, and $^{109}$Pd. Indium 112 ($^{112}$In) is a preferred isotope in the case where in vivo imaging is employed.

Examples of suitable fluorescent labels include $^{152}$Eu label, fluorescein label, isothiocyanate label, rhodamin label, phycoerythrin label, phycocyanin label, allophycocyanin label, o-phthalaldehyde label, and fluorescamine label.

Examples of suitable marker toxins include diphtheria toxin, ricin, and cholera toxin. Examples of chemiluminescent labels include luminal label, isoluminal label, aromatic acridinium ester label, imidazole label, acridinium salt label, oxalate ester label, luciferin label, luciferase label, and aequorin label.

Representative techniques for binding the above-mentioned labels to antibodies are provided by Kennedy et al., Clin. Chim. Acta 70: 1-31 (1976) and Schurs et al., Clin. Chim. Acta 81: 1-40 (1977).

Method of the Present Invention

The present invention, preferably, intends to cover the following individual, whose biological sample is diluted 10-fold or more and yet enables an antibody against the small protein encoded by the intermediate stage transcript of HHV-6 (SITH-1) to be detected by an immunological detection method using immunological antigen-antibody technique.

The present invention aims to achieve any one of the following purposes by administering a human herpesvirus 6 suppressor to the individual;

a) treating or preventing mood disorders;

b) suppressing an elevation of the level of SITH-1 within cells in the brain of the individual, reducing the number of cells in the brain that carry the protein SITH-1, and/or reducing the total amount of SITH-1 in the brain;

c) suppressing an elevation of the level of a calcium modulating cyclophilin ligand (CAML) protein within cells in the brain of the individual; or d) suppressing an elevation of the level of calcium ions within cells in the brain of the individual.

The present invention encompasses the following as preferred modes.

1. A method for treating or preventing mood disorders, which comprises administering a human herpesvirus 6 suppressor to the following individual, whose biological sample is diluted 10-fold or more and yet enables an antibody against the small protein encoded by the intermediate stage transcript of HHV-6 (SITH-1) to be detected by an immunological detection method using immunological antigen-antibody technique.

2. A method for administering a human herpesvirus 6 suppressor to the following individual, whose biological sample is diluted 10-fold or more and yet enables an antibody against the small protein encoded by the intermediate stage transcript of HHV-6 (SITH-1) to be detected by an immunological detection method using immunological antigen-antibody technique, thereby suppressing an elevation of the level of SITH-1 within cells in the brain of the individual, reducing the number of cells in the brain that carry the protein SITH-1, and/or reducing the total amount of SITH-1 in the brain.

3. A method for administering a human herpesvirus 6 suppressor to the following individual, whose biological sample is diluted 10-fold or more and yet enables an antibody against the small protein encoded by the intermediate stage transcript of HHV-6 (SITH-1) to be detected by an immunological detection method using immunological antigen-antibody technique, thereby suppressing an elevation of the level of a calcium modulating cyclophilin ligand (CAML) protein within cells in the brain of the individual.

4. A method for administering a human herpesvirus 6 suppressor to the following individual, whose biological sample is diluted 10-fold or more and yet enables an antibody against the small protein encoded by the intermediate stage transcript of HHV-6 (SITH-1) to be detected by an immunological detection method using immunological antigen-antibody technique, thereby suppressing an elevation of the level of calcium ions within cells in the brain of the individual.

5. The method according to any one of embodiments 1 to 4 wherein the individual whose biological sample is diluted 10-fold or more and yet enables an antibody against the small protein encoded by the intermediate stage transcript of HHV-6 (SITH-1) to be detected by an immunological detection method using immunological antigen-antibody technique, is i) a patient with mood disorder or ii) an individual who is likely to suffer from mood disorder.

6. The method according to any one of embodiments 1 to 4, wherein the human herpesvirus 6 suppressor is an anti-human herpesvirus 6 drug (anti-HHV-6 drug) or a virus reactivation suppressor.

7. The method according to embodiment 6, wherein the anti-HHV-6 drug is selected from the group consisting of acyclovir, ganciclovir, valganciclovir, foscarnet, famciclovir, and idoxuridine (IDU).

8. The method according to embodiment 6, wherein the virus reactivation suppressor is selected from the group consisting of D-ribose, vitamin C, and an active hexose correlated compound (AHCC).

9. The method according to any one of embodiments 2 to 4, wherein the cells in the brain are glial cells.

10. The method according to any one of embodiments 1 to 4, wherein the biological sample is selected from the group consisting of blood, serum, cerebrospinal fluid, saliva, sweat, lymph, and breast milk.

11. The method according to any one of embodiments 1 to 4, wherein SITH-1 is encoded by the following nucleic acids:
   (1) a nucleic acid coding for a protein comprising the amino acid sequence of SEQ ID NO:1;
   (2) a nucleic acid coding for a protein comprising an amino acid sequence that is at least 80% identical to the amino acid sequence of SEQ ID NO:1 and having a biological activity of SITH-1;
   (3) a nucleic acid comprising the nucleotide sequence of SEQ ID NO:2; and
   (4) a nucleic acid which hybridizes with a nucleic acid comprising a nucleotide sequence complementary to the nucleotide sequence of SEQ ID NO:2 under stringent hybridizing conditions and which has a biological activity of SITH-1.

12. A method for treating or preventing mood disorders, which comprises administering a human herpesvirus 6 suppressor to the following individual, whose biological sample contains more amount of the small protein encoded by the intermediate stage transcript of HHV-6 (SITH-1) and/or an antibody thereof than that of a healthy subject.

13. A method for treating or preventing mood disorders, which comprises administering the following individual, i) a patient with mood disorder or ii) an individual who is likely to suffer from mood disorder, with a human herpesvirus 6 suppressor, or an agent that suppresses the human herpesvirus 6 infection, proliferation, latent infection and/or reactivation.

The "treatment" as used herein covers eliminating or alleviating symptoms of mood disorders and suppressing them from worsening. The "prevention" as used herein covers suppressing or retarding the manifestation of symptoms of mood disorders.

On the following pages, the present invention is described specifically.

I) Individuals to be Taken Care of by the Invention

In one embodiment a subject of the present invention can be i) a patient with mood disorder or ii) an individual who is likely to suffer from mood disorder.

The "patient with mood disorder" refers to patients (humans) who are experiencing abnormally depressive or elated feelings to suffer from such a state that their social life functioning or daily life functioning is being disabled. Medically, operational diagnoses are performed in accordance with the diagnostic criteria specified either by the DSM (Diagnostic and Statistical Manual of Mental Disorders), as introduced by the American Psychiatric Association, or by the ICD (the International Classification of Disease).

"Patients with mood disorder" also include patients who present with symptoms of mood disorder that are caused by other, "non-psychiatric" diseases. In addition, "patients with mood disorder" may also include patients with CFS who manifest symptoms of mood disorder.

The "individual who is likely to suffer from mood disorder" means a person who is not definitely judged to be among "patients with mood disorder" but who is diagnosed to have high likelihood for becoming such a patient with mood disorder. This may be exemplified by a case where the relevant DSM or ICD diagnostic criteria are not met because the period during which the social life functioning or daily life functioning is being disabled on account of the already mentioned variations in mood is not longer than two weeks or because the symptoms are so mild that it cannot be said definitely that the social life functioning or daily life functioning is being completely disabled.

Alternatively, a person who has not yet manifested mood disorder but who is diagnosed to have a higher possibility than average to become a patient with mood disorder in the future on account of genetic aberrations in the individual, his or her life history, character, family life, etc. may be diagnosed as an "individual who is likely suffer from mood disorder."

The method of the present invention is also effective for treating or preventing mood disorders in individuals of the state described above. Alternatively, persons who have no distinct symptoms of mood disorders that can be observed are also taken care of by the method, and prevention of symptoms of mood disorders is also covered by the method of the present invention.

The "patient with mood disorder" and the "individual who is likely to suffer from mood disorder" are herein sometimes collectively referred to as the "patient with mood disorder."

Certain aspects of the present invention are directed to the treatment of patients who have been diagnosed as suffering from a mood disorder, where conventional agents for treating the mood disorder have not been effective, and where an antibody to SITH-1 protein can be detected in a biological sample taken from the patient.

In a non-limiting case, the present invention intends to cover individuals wherein HHV-6 expresses SITH-1 in cerebral glial cells, and more preferably, individuals wherein HHV-6 highly expresses SITH-1 in cerebral glial cells Further, in a non-limiting case, the method of the present invention preferably intends to cover individuals whose biological sample is examined for an antibody titer against the protein SITH-1, and shows (significantly) higher antibody titer compared to the average of healthy subjects. More preferably, the present invention intends to cover the following individuals whose biological sample is diluted 10-fold or more and yet enables an antibody against the small protein encoded by the intermediate stage transcript of HHV-6 (SITH-1) to be detected by an immunological detection method using immunological antigen-antibody technique. The "individuals whose biological sample shows (significantly) higher antibody titer" and "individuals whose biological sample enables an antibody against the small protein encoded by the intermediate stage transcript of HHV-6 (SITH-1) to be detected by an immunological detection method" encompass the "individuals whose biological sample showed (significantly) higher antibody titer" and "individuals whose biological sample enabled an antibody against the small protein encoded by the intermediate stage transcript of HHV-6 (SITH-1) to be detected by an immunological detection method" when determination has been actually performed, as well as individuals if can show such result when determination is performed.

Healthy subject refers to a person without any symptoms of a mood disorder, and preferably, when a serum sample taken from said person is diluted 10-fold no antibody against the protein SITH-1 is detected using an indirect fluorescent antibody technique where FITC is used as a fluorescent agent.

As an immunological detection method using immunological antigen-antibody technique, any known immunological detection method can be used. Preferably, an indirect fluorescent antibody technique can be used.

The present invention naturally covers individuals whose biological sample is detected to contain more amount of the protein SITH-1 per se than a healthy subject. The amount of the protein SITH-1 detected in such individuals are (significantly) greater than the average of healthy subjects. "(significantly) greater" means more than one, preferably, two time or more", more preferably, "ten times or more". For detecting the protein SITH-1 in biological sample, any known methods similar to those to be used in case the antibody is detected, can be appropriately used. It is presumed that such individuals correspond to "a patient with mood disorder" or "an individual who is likely to suffer from mood disorder"

A detector of SITH-1 antibody means any substance which can specifically detect the SITH-1 antibody by an immunological detection method. Preferably, the detector may be a protein or a polypeptide recognized by the SITH-1 antibody, or a partial fragment thereof. The "partial fragment" preferably contains at least an epitope-carrying peptide. In a preferred embodiment, the detector may be the protein SITH-1, or a partial fragment thereof.

Since measuring the titer of antibodies against the protein SITH-1 enables determining whether HHV-6 has expressed the protein SITH-1 in cerebral glial cells of the individual, estimate can be made whether the mood disorder involved is due to SITH-1 or if the person is highly likely to develop a mood disorder in the future on account of SITH-1; as a result, it can be judged more positively as to whether the administration of the human herpesvirus 6 suppressor will be effective in treating or preventing mood disorder.

The antibody titer against SITH-1 can be measured by any known methods. In addition, the methods described in the international application of prior filing can be utilized. Examples include an indirect fluorescent antibody technique, an ELISA technique, western blotting, a particle agglutination technique, and a nanotechnology-based technique.

The biological sample is not particularly limited as long as it is derived from living organisms that allow for determination of antibody titers. Preferably, it is selected from the group consisting of blood, serum, cerebrospinal fluid, saliva, sweat, lymph, and breast milk. Blood, serum or cerebrospinal fluid is more preferred.

Consider, for example, the use of an indirect fluorescent antibody technique using FITC (fluorescent isothiocyanate) as a fluorescent agent, the individual to be taken care of in this case is one whose biological sample is diluted at least 10-fold, preferably at least 20-fold and yet allows for detection of an antibody against the protein SITH-1. In a healthy person, even a 10-fold dilution does not allow for antibody detection.

The antibody titer against SITH-1 can also be measured by a method other than an indirect fluorescent antibody technique. As for the antibody titer obtained by a method other than an indirect fluorescent antibody technique, the detection results of the method and the indirect fluorescent antibody technique are compared, and then individuals who can be the subject of the present invention, that is, individuals showing (significantly) higher antibody titer compared to the average of healthy subjects can easily be identified.

II) Mechanisms of Action in the Method of the Invention

The present inventors found that the amount of expression of SITH-1 was suppressed by administering ganciclovir, a kind of human herpesvirus 6 suppressors, and this has led to conception of the present invention. Hence, the method of the present invention treats or prevents mood disorders as mediated by the following mechanisms of action in response to the administration of the human herpesvirus 6 suppressor.

i) By the action of the human herpesvirus 6 suppressor, the human herpesvirus 6 infection, proliferation, latent infection and/or reactivation within cells in the brain of an individual is suppressed;

ii) An elevation of the level of a small protein encoded by the intermediate stage transcript of HHV-6 (SITH-1) within cells in the brain of the individual is suppressed, the number of cells in the brain that carry the protein SITH-1 is reduced, and/or the total amount of the protein SITH-1 in the brain is reduced;

iii) An elevation of the level of a calcium modulating cyclophilin ligand (CAML) protein within cells in the brain of the individual is suppressed; or iv) An elevation of the level of calcium ions within cells in the brain of the individual is suppressed.

The cells in the brain are glial cells, by which are meant all kinds of glial cells including mature and precursor forms of glial cells in the central nervous system, as exemplified by astrocytes, oligodendrocytes, microglias, and ependymal cells. Other types that may be embraced are satellite cells, Schwann cells and terminal gliocytes in the peripheral nervous system.

The phrase reading "an elevation is suppressed" which appears in ii) to iv) above is not particularly limited but it preferably intends cases of at least 10%, 20%, 30%, 40%, 50%, 60%, 70% or 80% suppression.

The expression reading "the number of cells in the brain that carry the protein SITH-1 is reduced" which appears in ii) is not particularly limited but it preferably intends cases where the cell count is suppressed by at least 10%, 20%, 30%, 40%, 50%, 60%, 70% or 80%.

The "level of protein SITH-1 within cells in the brain" which appears in ii) can be measured by a known method of measuring protein levels. Specifically, accurate measurement is possible by biopsy on brain cells. The "number of cells in the brain that carry the protein SITH-1" can also be measured by biopsy on brain cells. An increase or decrease in "the total amount of the protein SITH-1 in the brain" can be evaluated by measuring the quantity of antibodies (antibody titers) in cerebrospinal fluid that are produced in response to SITH-1 in the brain. If cerebrospinal fluid is difficult to sample, an increase or decrease in the titer of anti-SITH-1 antibodies in blood may be measured to know the change in the total amount of the protein SITH-1 within cells in the brain since the amount of expression of SITH-1 in the brain is also reflected in the antibody titers in the blood.

The "level of CAML protein within cells in the brain" which appears in iii) can be measured accurately by a known method, say, biopsy. In addition, the human herpesvirus 6 suppressor used in the present invention decreases the total amount of the protein SITH-1 in the brain, so unless it is a chemical that has a brain cell specific action, it suppresses an elevation of the CAML protein level within cells in the brain while, at the same time, it suppresses an elevation of the CAML protein level within macrophages in the peripheral system. Therefore, by measuring the CAML protein level within macrophages in the peripheral system, the suppression of an elevation of the CAML protein level within cells in the brain can be evaluated.

The "level of calcium ions within cells in the brain of an individual" which appears in iv) can be measured accurately by a known method, say, biopsy. In addition, unless it is a chemical that has a brain cell specific action, the human herpesvirus 6 suppressor used in the present invention reduces the total amount of the protein SITH-1 in the brain to eventually suppress an elevation of the CAML protein level within cells in the brain; hence, it suppresses an elevation of the level of calcium ions within cells in the brain while, at the same time, it suppresses an elevation of the level of calcium ions within macrophages in the peripheral system. Therefore, by measuring the level of calcium ions within macrophages in the peripheral system, the suppression of an elevation of the level of calcium ions within cells in the brain can be evaluated.

Remember that Non-Patent Document 6 reports the findings of a study, in which "patients who were presenting with encephalitis/encephalopathy-like symptoms and long-standing fatigue symptoms, presumably due to the infection with HHV-6 or Epstein-Barr virus (EBV), were administered with the anti-herpes viral agent valganciclovir, with the result of an improvement in their symptoms." Now that Non-Patent Document 6 is reviewed after the conception of the present invention, it can be understood that it supports the above-described mechanism that has been discovered by the present inventors.

This may be explained as follows: the cause of the depressive symptoms as manifested in those patients was the protein SITH-1 expressed by HHV-6 latently infecting the glial cells in their brains, and since its proliferation was suppressed by valganciclovir, HHV-6 could no longer maintain the number of the latently infected cells that were capable of expressing SITH-1 in the brain, with the result that the number of those cells was sufficiently decreased to achieve an improvement in the symptoms. This mechanism of action was only clarified after the present invention was conceived of.

III) Human Herpesvirus 6 Suppressor

According to the present invention, a patient with mood disorder is administered with a human herpesvirus 6 suppressor, or an agent that suppresses the human herpesvirus 6 infection, proliferation, latent infection and/or reactivation, whereby the mood disorder he or she is suffering from is treated or diagnosed.

Herpes viruses can pass through four stages of their life cycle, cell infection, latent infection, proliferation, and reactivation. Therefore, the human herpesvirus 6 suppressor suppresses one or more of these stages. The human herpesvirus 6 suppressor is not limited to any particular types and any substances known as agents for medical applications can be employed.

Preferably, the human herpesvirus 6 suppressor is an anti-human herpesvirus 6 drug (anti-HHV-6 drug) or a virus reactivation suppressor.

Mechanism of function of the anti-HHV-6 drug is not particularly limited. Examples of a anti-HHV-6 drug may include virus DNA polymerase inhibitor, protease inhibitor, terminal transferase inhibitor, helicase inhibitor and the like.

Preferably, the anti-HHV-6 agent is selected from the group that consists of, but is not limited to, acyclovir (GlaxoSmithKline), ganciclovir (Syntex), valganciclovir (F. Hoffmann La-Roche), foscarnet (AstraZeneca), famciclovir (Novartis), and idoxuridine (IDU) (The Journal of Immunology, 1964, 92: 550-554; Effects of 5-Iodo-2-Desoxyuridine (IDU) on Herpesvirus Synthesis and Survival in Infected Cells, Kendall O. Smith and C. Dean Dukes.)

Ganciclovir and valganciclovir are more preferred. From the viewpoints of less side effects and sustained release, valganciclovir is most preferred. Each of those compounds is known and is readily available to skilled artisans or can be manufactured by them.

The virus reactivation suppressor should be capable of not only directly suppressing virion formation or viral replication but also suppressing their preparatory stages, for example, gene expression at the intermediate stage. The virus replication suppressor is selected from the group that consists of, but not limited to, D-ribose, vitamin C and an active hexose correlated compound (AHCC (AMINO UP CHEMICAL)).

Further, many of materials having antioxidant action or anti-fatigue action can also suppress virus reactivation. These materials can also preferably be used. The efficacy of these compounds is mild but none of them have strong side effects, so their continuous administration is easy to realize. They can be used for mild improvement of the symptoms of patients with mood disorder, and even for the prevention of manifestation of symptoms of mood disorders by being administered to persons who may have high or low antibody titers against SITH-1 but who certainly do not have any symptoms of mood disorders.

These agents may preferably be administered together with one or more pharmaceutically acceptable carriers. The pharmaceutically acceptable carriers may be pharmaceutically acceptable diluents, fillers, adjuvants, excipients and vehicles that may be determined for specific routes of administration, as well as water- or oil-based liquid suspensions that may be formulated using suitable dispersants, wetting agents, or suspending agents.

The pharmaceutically acceptable carriers are generally aseptic, are not pyrogenic, and include water, oils, solvents, salts, saccharides, as well as other carbohydrates, emulsifiers, buffers, antimicrobial agents, and chelatants. Specific types of pharmaceutically acceptable carriers and the ratio of the active compound to the carrier are determined by the solubility and chemical characteristics of the composition, the mode of its administration, and the standard pharmaceutical practices.

The human herpesvirus 6 suppressor is administered to patients in a mode as appropriate for its kind. For example, it may be administered intravenously, transcutaneously, intradermally, intraperitoneally, intramuscularly, intranasally, epidurally, perorally, topically, subcutaneously, or by any other suitable technique. Preferably, it is administered intravenously or intraperitoneally. An optimum drug formulary can be readily determined in accordance with the intended route of administration, mode of transport, and the desirable dosage.

The amount of the human herpesvirus 6 suppressor to be administered depends on age, the condition to be treated, body weight, the desirable duration of treatment, the method of administration, and other parameters. The effective dose is routinely determined by doctors or other qualified medical experts. Preferably used is the dosage that is commonly provided as a human herpesvirus 6 suppressor.

As a non-limiting example, commercially available human herpesvirus 6 suppressors can preferably be used by an appropriate method and dose as described in a manufacturer's instructions. Without any limitation, acyclovir can be administered, for example, perorally, 200 mg/time, five times per day for an adult. Ganciclovir can be administered for example, 5 mg/kg body weight/time, two times intravenous drip infusion per day for an adult. Famciclovir can be administered perorally, 500 mg/time, three times per day for an adult. Valganciclovir can be administered perorally, 900 mg/time, two times per day for an adult.

IV) On the Protein SITH-1 and the Associated Nucleic Acids

As used herein, the protein SITH-1 is preferably encoded by the following nucleic acids:

1) a nucleic acid coding for a protein comprising the amino acid sequence of SEQ ID NO:1;
2) a nucleic acid coding for a protein comprising an amino acid sequence that is at least 80% identical to the amino acid sequence of SEQ ID NO:1 and having a biological activity of SITH-1;
3) a nucleic acid comprising the nucleotide sequence of SEQ ID NO:2; and
4) a nucleic acid which hybridizes with a nucleic acid comprising a nucleotide sequence complementary to the nucleotide sequence of SEQ ID NO:2 under stringent hybridizing conditions and which has a biological activity of SITH-1.

SITH-1 (of native type) may typically be a protein comprising the amino acid sequence of SEQ ID NO:1 or a protein encoded by a nucleic acid comprising the nucleotide sequence of SEQ ID NO:2. Alternatively, SITH-1 may be a variant of the protein comprising the amino acid sequence of SEQ ID NO:1 or the protein encoded by a nucleic acid comprising the nucleotide sequence of SEQ ID NO:2, provided that it has a biological activity of SITH-1.

In the present invention, the "biological activity" of SITH-1 means to encompass biological activities like "elevating the level of CAML protein", "elevating the intracellular calcium level" or the like.

The variant of SITH-1 may be a protein comprising an amino acid sequence having one or more amino acid deletions, substitutions, insertions and/or additions introduced in the amino acid sequence of SEQ ID NO:1, provided that it has a biological activity of SITH-1. The substitution may be a conservative substitution, in which a given amino acid residue is replaced by a residue having similar physicochemical characteristics, and non-limiting examples of the conservative substitution include substitution of one aliphatic-group containing amino acid residue (e.g., Ile, Val, Leu or Ala) for another, and substitution of one polar residue for another, as between Lys and Arg, or Glu and Asp, or Gln and Asn.

The variation due to amino acid deletions, substitutions, insertions and/or additions can be constructed from DNA coding for the native protein by applying a well-known technique, say, site-specific mutagenesis (see, for example, Nucleic Acid Research, Vol. 10, No. 20, p. 6487-6500, 1982, which is incorporated herein by reference in its entirety). As used herein, the expression "one or more amino acids" means a sufficient number of amino acids that can be deleted, substituted, inserted and/or added by site-specific mutagenesis. It should also be noted that the expression "one or more amino acids" as used herein may sometimes mean one or several amino acids.

Site-specific mutagenesis may be performed as follows using synthetic oligonucleotide primers that are complementary to the single-stranded phage DNA to be mutated, except for a specific mismatch that corresponds to the desirable mutation. To be more specific, the above-mentioned synthetic oligonucleotide primers are used to get a phage to synthesize the intended complementary strand and a host cell is transformed with the resulting double-stranded DNA. A culture of the transformed cell is plated on agar and plaques are formed from the phage-containing single cells. Theoretically, 50% of the new colonies contain phages having a single-stranded mutation and the remaining 50% have the original sequence. The obtained plaques are hybridized with a synthetic probe, as labeled by kinase treatment, at a temperature that allows for hybridization with those colonies that exhibit complete match with DNA having the above-mentioned desirable mutation but that does not allow for hybridization with those colonies having the original strand. Subsequently, plaques that hybridize with that probe are picked and cultured for DNA recovery.

Note that the methods of introducing one or more amino acid deletions, substitutions, insertions and/or additions in the amino acid sequence of a biologically active peptide while retaining its activity include not only the above-described site-specific mutagenesis but also a method that involves treating the gene with a mutagen, as well as a method that comprises cleaving the gene selectively, then removing, substituting, inserting or adding a chosen nucleotide, and finally linking the cleaved fragments. More preferably, SITH-1 as used in the present invention is a protein comprising an amino an amino acid sequence having one to ten amino acid deletions, substitutions, insertions or additions introduced in the amino acid sequence of SEQ ID NO:2, provided that it has a biological activity of SITH-1.

The variant of SITH-1 may also be a protein comprising an amino acid sequence that is at least 80% identical, preferably at least 85% identical, at least 90% identical, at least 95% identical, at least 96% identical, at least 97% identical, at least 98% identical, or at least 99% identical, and more preferably at least 99.3% identical, to the amino acid sequence of SEQ ID NO:2 and which has a biological activity of SITH-1.

Percent identity between two amino acid sequences may be determined by visual inspection and mathematical calculation. Alternatively, the percent identity of two protein sequences can be determined by comparing sequence information using the GAP computer program that is based on the algorithm of Needleman, S. B. and Wunsch, C. D. (J. Mol. Biol., 48: 443-453, 1970) and which is available from the University of Wisconsin Genetics Computer Group (UWGCG). The preferred default parameters for the GAP program include: (1) a scoring matrix, blosum62, as described by Henikoff, S. and Henikoff, J. G. (Proc. Natl. Acad. Sci. USA 89:10915-10919, 1992); (2) a gap weight of 12; (3) a gap length weight of 4; and (4) no penalty for end gaps.

Other programs used by one skilled in the art of sequence comparison may also be used. Percent identity can be determined by comparison with sequence information using the BLAST program descried in, for example, Altschul et al. (Nucl. Acids. Res., 25, p. 3389-3402, 1997). This program can be accessed from the Internet at the website of the National Center for Biotechnology Information (NCBI) or the DNA Data Bank of Japan (DDBJ). Various conditions (parameters) for identity search by the BLAST program are detailed at that website and part of the settings can be varied as appropriate, although search is typically performed using the default values. Alternatively, percent identity between two amino acid sequences may be determined by a program such as the genetic information processing software GENETYX Ver. 7 (Genetyx) or the FASTA algorithm. In this alternative case, search may be performed using the default values.

The percent identity of two nucleotide sequences may be determined by visual inspection and mathematical calculation, or more preferably by comparing sequence information using a computer program. A typical, preferred computer program is the Wisconsin package, the program GAP of version 6.0, of Genetics Computer Group (GCG; Madison, State of Wisconsin) (Devereux et al., Nucl. Acids Res. 12:387, 1984). Using this program GAP, one can perform comparison not only between two nucleic acid sequences but also between two amino acid sequences and between a nucleic acid sequence and an amino acid sequence. Here, the preferred default parameters for the program GAP include: (1) GCG implementation of a unary comparison matrix (containing a value of 1 for identities and 0 for non-identities) for nucleotides, and the weighted amino acid comparison matrix of Gribskov and Burgess, Nucl. Acids Res. 14:6745, 1986, as described by Schwartz and Dayhoff, eds., Atlas of Polypeptide Sequence and Structure, National Biomedical Research Foundation, pp. 353-358, 1979, or other applicable comparison matrices; (2) a penalty of 30 for each amino acid gap and an additional 1 penalty for each symbol in each gap, or a penalty of 50 for each gap in a nucleotide sequence and an additional 3 penalty for each symbol in each gap; (3) no penalty for end gaps; and (4) no maximum penalty for long gaps. Other sequence comparison programs that are used by skilled artisans and which may be used in the present invention include the BLAST program, version 2.2.7, that can be downloaded from the website of the US National Library of Medicine, or the UW-BLAST 2.0 algorithm. Settings of standard default parameters for UW-BLAST 2.0 are described at the following website: http://blast.wustl.edu. In addition, the BLAST algorithm uses the amino acid scoring matrix BLOSUM 62 and the selection parameters that can be used are as follows: (A) inclusion of a filter for masking segments of query sequence having low compositional complexity (as determined by the SEG program of Wootton and Federhen (Computers and Chemistry, 1993); see also Wootton and Federhen, "Analysis of compositionally biased regions in sequence databases" in Methods Enzymol., 266: 544-71, 1996) or for masking segments comprising internal repeats of short periodicity (as determined by the XNU program of Claverie and States (Computers and Chemistry, 1993)); and (B) expected probabilities of a match that is to be found merely by chance in accordance with a statistic model of thresholds, or E-scores (Karlin and Altschul, 1990), of statistically significant differences for reporting a match with database sequences (if a statistically significant difference due to a certain match is greater than an E-score threshold, the match is not reported); the numerical value of a preferred E-score threshold is either 0.5 or, in increasing order of preference, 0.25, 0.1, 0.05, 0.01, 0.001, 0.0001, 1e-5, 1e-10, 1e-15, 1e-20, 1e-25, 1e-30, 1e-40, 1e-50, 1e-75, or 1e-100.

The variant of SITH-1 may also be a protein that is encoded by a nucleic acid comprising a nucleotide sequence that hybridizes with a strand complementary to the nucleotide sequence of SEQ ID NO:2 under stringent conditions, provided that the protein has a biological activity of SITH-1.

The phrase "under stringent conditions" as used herein means hybridizing under conditions of moderate or high stringency. Specifically, conditions of moderate stringency can be readily determined by those having ordinary skill in the art based on, for example, the length of DNA. The basic conditions are set forth by Sambrook et al. in Molecular Cloning: A Laboratory Manual, 3rd ed. Chapter 6, Cold Spring Harbor Laboratory Press, 2001, and include use of: a pre-washing solution of 5×SSC, 0.5% SDS, and 1.0 mM EDTA (pH 8.0); hybridizing conditions of about 50% formamide, 2×SSC-6×SSC, preferably 5-6×SSC and 0.5% SDS, at about 42° C. (or other similar hybridization solutions, such as Stark's solution in about 50% formamide at about 42° C.); and washing conditions of about 50-68° C., 0.1-6×SSC, and 0.1% SDS. Preferably, conditions of moderate stringency include hybridizing conditions of about 50° C., 6×SSC, and 0.5% SDS. Conditions of high stringency can also be readily determined by the skilled artisan based on, for example, the length of DNA.

Generally, such conditions include hybridization at higher temperatures and/or at lower salt concentrations than the conditions of moderate stringency (e.g., hybridization in the presence of about 0.5% SDS at about 65° C. with 6×SSC to 0.2×SSC, preferably 6×SSC, more preferably 2×SSC, even more preferably 0.2×SSC, or 0.1×SSC) and/or washing, and may be defined as hybridizing conditions of the type described above, and involving washing at approximately 65-68° C. in 0.2-0.1×SSC and 0.1% SDS. In the buffer solution for use in hybridization and washing, SSC (1×SSC consists of 0.15 M NaCl and 15 mM sodium citrate) may be replaced by SSPE (1×SSPE consists of 0.15 M NaCl, 10 mM $NaH_2PO_4$, and 1.25 mM EDTA; pH 7.4), and washing is performed for about 15 minutes to one hour after hybridization is complete.

If desired, a commercial hybridization kit may be employed that does not use a radioactive substance as the probe. A specific example is hybridization that employs an ECL direct labeling & detection system (product of Amersham). Stringent hybridization may be performed at 42° C. for 4 hours after a blocking reagent and NaCl are added in respective amounts of 5% (w/v) and 0.5 M to the hybridization buffer in the kit; washing may be performed twice in 0.4% SDS and 0.5×SSC for 20 minutes each at 55° C., then once in 2×SSC for 5 minutes at room temperature.

EXAMPLES

On the following pages, the present invention is described in greater detail by reference to examples, which are given here for illustrative purposes only and will by no means limit the present invention. The scope of the present invention shall be interpreted on the basis of the descriptions in the accompanying claims. Further, it should be easy for skilled artisans to modify or otherwise change the following examples on the basis of the foregoing disclosures in the specification.

Reference Example

1. Identification of Gene Products (mRNA) Coding for the Latent Infection Specific Protein SITH-1

Messenger RNA (mRNA) was separated from those macrophages described in Non-Patent Document 1 that were latently infected with HHV-6 and a reverse transcription reaction was performed using random primers, IE4RB as a primer for reverse transcription of sense transcripts, and IE2FB as a primer for reverse transcription of anti-sense transcripts. Thereafter, the reverse transcripts (cDNA) were amplified by the PCR technique using the primers IE4RB and IE2FB and the products were further amplified by the double-nested PCR technique using the inner primers IE4RA and IE2FA. FIG. 1 shows the correspondence between the sense transcript (H6LT) of the known mRNA during productive infection and the novel latent infection specific gene product, as well as the open reading frame of the latent infection specific protein SITH-1. For details of the sequence information about SITH-1 and the novel latent infection specific gene, see the SEQUENCE LISTING As a result, a 925-bp product was amplified and it differed both from the 351-bp product amplified from the mRNA being expressed in MT-4 cells that were productively infected with HHV-6 and from the 351-bp product amplified from the latent infection specific gene product (HHV-6 latency-associated transcript: H6LT) that was detectable during the latent infection of macrophages (MΦ) with HHV-6.

Figure 2:
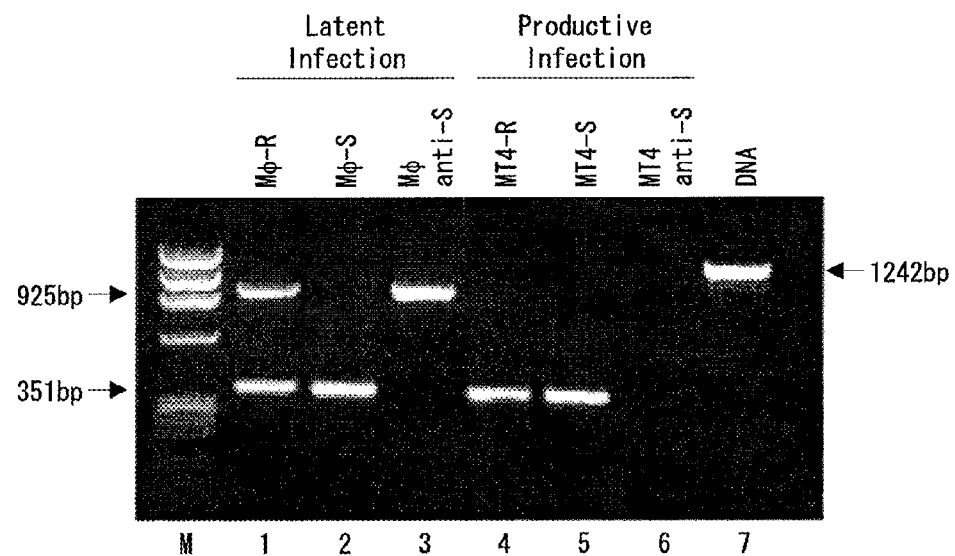
FIG. 2 is a diagram showing the results of amplification of HHV-6 gene products by the PCR technique.

Since this product was also different from the 1241-bp amplification product from HHV-6 DNA in that it was solely amplified from the product of reverse transcription of anti-sense transcripts in the cells latently infected with HHV-6, it was shown to be a heretofore unknown, novel latent infection specific gene product (see FIG. 2). In FIG. 2, R signifies a random primer, S, a sense transcript, and anti-S, an anti-sense transcript.

Figure 3:
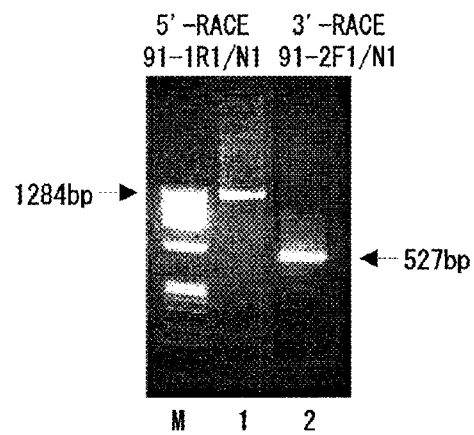
FIG. 3 is a diagram showing the results of analyzing novel latent infection specific gene mRNAs by the RACE technique.

To determine the structure of this novel latent infection specific gene mRNA, the 5'-rapid amplification of cDNA ends (RACE) method and the 3'-RACE method were performed, whereby not only the 5'- and 3'-ends but also the overall nucleotide sequence was determined (see FIG. 3).
IE4RB:    5'-GATGCTCCTTCTTCCACATTACTGG-3' (SEQ ID NO:4)
IE2FB:    5'-CATCCCATCAATTATTGGATTGCTGG-3' (SEQ ID NO:5)
IE2FA:    5'-GAAACCACCACCTGGAATCAATCTCC-3' (SEQ ID NO:6)
IE4RA: 5'-GACACATTCTTGGAAGCGATGTCG-3' (SEQ ID NO:7)
N1:  5'-GCTGGGTAGTCCCCACCTTTCTAGA-3' (SEQ ID NO:8)
α5'-CTGAAGCATGTAAGCACATCTCTTGC-3' (SEQ ID NO:9)
αR1: 5'-GCTTCGAGATCAGTAGTGGTACG-3' (SEQ ID NO:10)

2. Functional Analysis of the Novel Latent Infection Specific Gene Protein SITH-1

Figure 4:
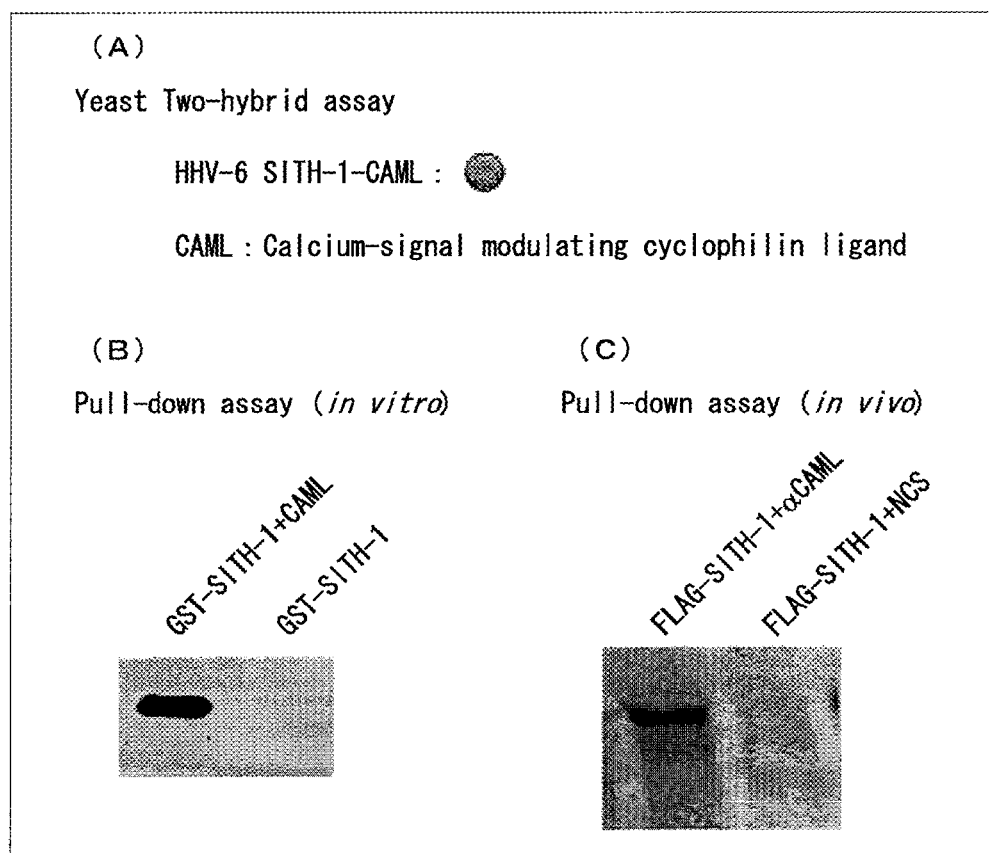
FIG. 4 is a diagram showing the results of an experiment in which a host protein binding to the protein SITH-1 was identified by the yeast two-hybrid assay.

To study the function of the protein SITH-1, a host protein to which the protein SITH-1 would bind within cells was identified. The method consisted of screening a human fetal brain cDNA library by the yeast two-hybrid assay with the protein SITH-1 used as a bait. The result is shown in FIG. 4: (A) yeast clones in which β-galactosidase was strongly expressed owing to binding between SITH-1 and CAML; (B) a diagram verifying by western blotting and staining of anti-CAML antibodies that in the in vitro pull-down assay, the CAML expressed in E. coli could be co-precipitated by means of the GST-SITH-1 fusion protein that was also expressed in E. coli and; (C) a diagram verifying by western blotting and staining of anti-FLAG antibodies that SITH-1 with a FLAG tag and CAML were introduced into 293T cells using an expression vector and that the SITH-1 could be co-precipitated by means of anti-CAML antibodies. As FIG. 4 shows, the protein SITH-1 was found to bind strongly to the calcium-signal modulating cyclophilin ligand (CAML).

CAML is a protein that has been reported to show strong expression in lymphocytes and in the brain and it is known to have the capacity to elevate the intracellular calcium level. Thus, in order to see whether the protein SITH-1 would be mediated by CAML to elevate the intracellular calcium level, both an astrocyte-like glial cell line (U373) in which SITH-1 had been expressed and untreated U373 cells were stained by the fluorescent antibody technique using anti-SITH-1 antibodies and anti-CAML antibodies. As it turned out, when the protein SITH-1 was expressed in the astrocyte-like glial cell line (U373), more CAML was found than in the untreated U373 cells (FIG. 5). The level of CAML expression in U373 cells was not very high when they were untreated but more CAML was found to occur by expressing SITH-1.

Figure 6:
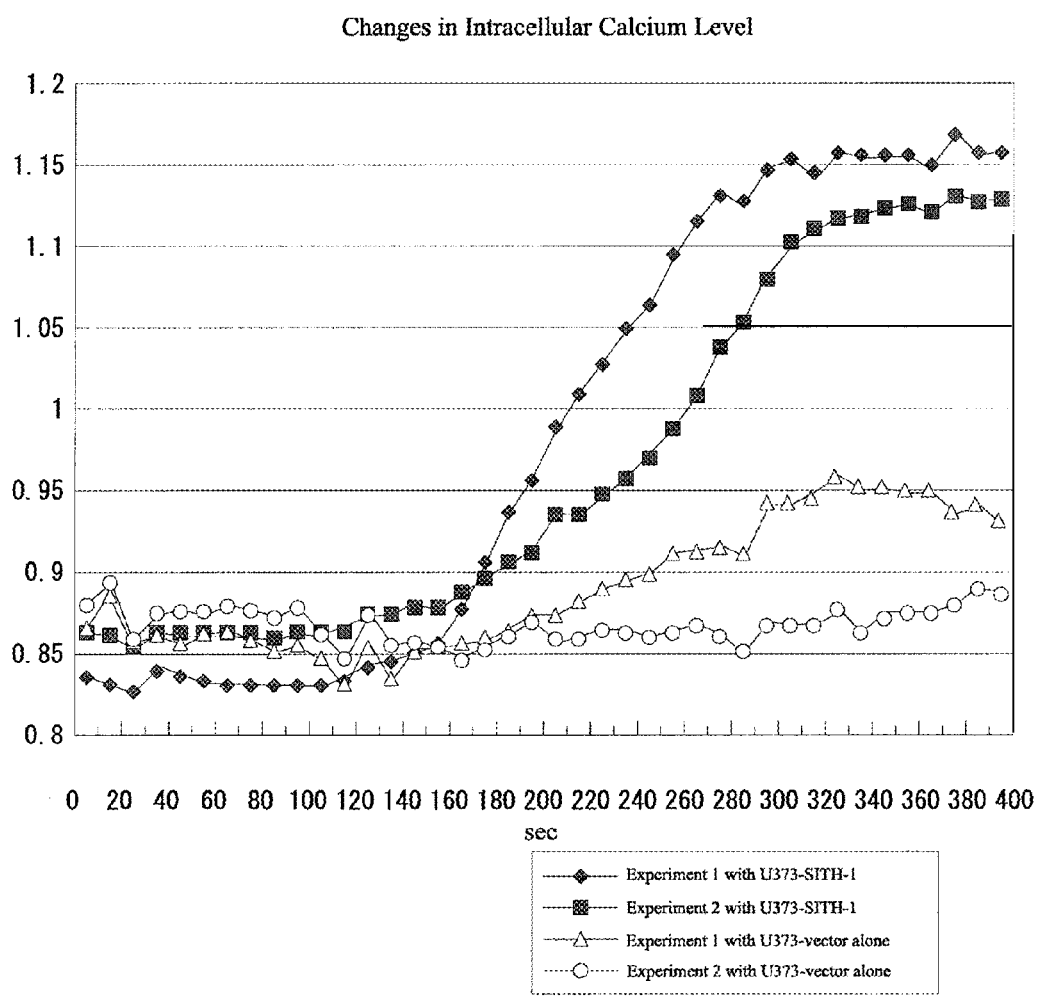
FIG. 6 is a diagram showing how SITH-1 elevated the calcium level in glial cells.

In another experiment, two samples were prepared; one sample was prepared by introducing SITH-1 into an astrocyte-like glial cell line (U373) via a retrovirus vector induced, and the other sample was prepared by introducing only the vector into the U373; each sample was stimulated with thapsigargin (TG) and the intracellular calcium level was measured using Fura2. As a result, the actual measurement of the intracellular calcium level showed that on account of stimulation with thapsigargin (TG), the intracellular calcium level in the SITH-1 expressing astrocyte-like glial cell line was considerably higher than in the cells into which only the vector had been introduced (FIG. 6).

From those results, it was found that the protein SITH-1 had the capacity to elevate the intracellular calcium level in the astrocyte-like glial cell line by being expressed during latent infection with HHV-6 to increase the amount of intracellular CAML.

3. Relationship Between SITH-1 and Mood Disorders

Figure 7:
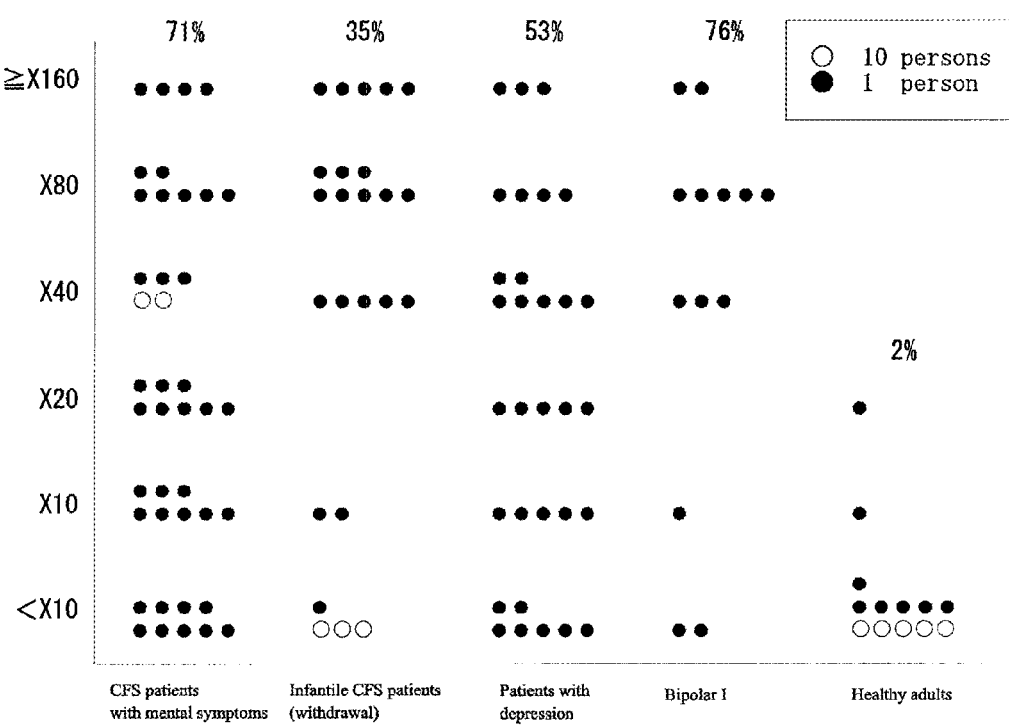
FIG. 7 is a graph showing the antibody titers to SITH-1 in patients with mental disorders.

In the next step, the present inventors studied the relationship between SITH-1 and mood disorders. The results are shown in FIG. 7. Unlike the latent infection specific gene protein reported in Non-Patent Document 5 and other prior art references, the antibody against SITH-1 was not closely related to patients with chronic fatigue syndrome but the frequency of antibody carriers was high among patients with mental disorders. In many cases, the patients with chronic fatigue syndrome (CFS) who also had psychiatric symptoms primarily manifested depressive symptoms whereas the infantile CFS patients mainly presented with abnormal agitation. In FIG. 7, "bipolar I" refers to patients with manic-depressive illness of severe symptoms. The healthy adults scarcely carried the antibody against SITH-1. For antibody titer measurement in serum, SITH-1 expressing 293T cells were used as antigens, and the FITC (fluorescent isothiocyanate) anti-human immunoglobulin antibody were uses as a second antibody. The indirect fluorescent antibody technique was then applied to examine antibody titer.

4. Construction 1 of Model Mice with Mental Disorder by Expressing SITH-1

SITH-1 to which a glial fibrillary acidic protein (GFAP) promoter was attached upstream of its open reading frame was injected into the brains of newborn mice using an adenovirus vector or a retrovirus vector. GFAP was a protein that would be specifically expressed in glial cells such as astrocytes. About 3 or 5 weeks after the injection, the behavior of the mice was observed to confirm the establishment of model mice with mental disorder by introduction of SITH-1.

Figure 8:
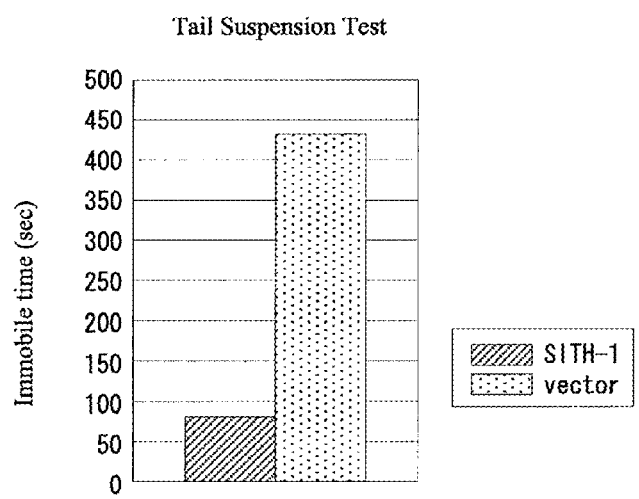
FIG. 8 is a graph showing the result of investigating the effect of SITH-1 in a tail suspension test.
Figure 9:
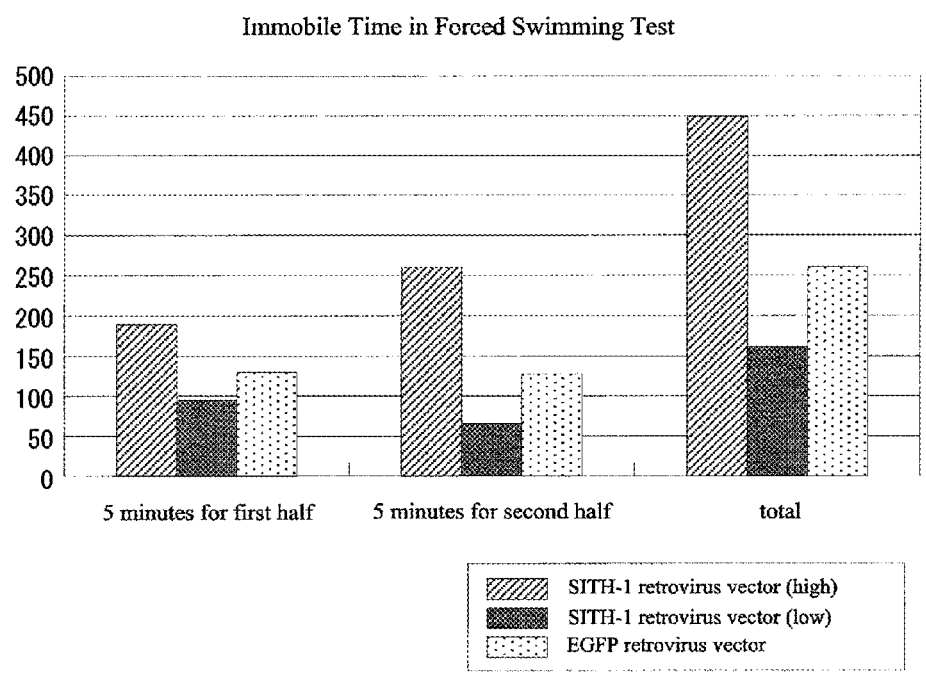
FIG. 9 is a graph showing the result of investigating the effect of SITH-1 in a forced swimming test.

A tail suspension test and a forced swimming test were conducted to evaluate mental disorders; these tests are commonly used to observe patients with depression or manic-depressive illness. Specifically, the mice transfected with SITH-1 using the adenovirus vector were subjected to a tail suspension test. As it turned out, the SITH-1 transfected mice had a markedly shorter immobile time, indicating that they were in a manic state (FIG. 8). Subsequently, the mice transfected with SITH-1 using the retrovirus vector were subjected to a forced swimming test. As it turned out, the mice transfected with the SITH-1 carrying retrovirus vector at HIGH titer had a longer immobile time than the control mice transfected with an enhanced green fluorescence protein (EGFP) gene, indicating that they were in a state of depression. In contrast, the mice transfected with the SITH-1 carrying retrovirus vector at LOW titer had a shorter immobile time, indicating that they were in a manic state (FIG. 9). Thus, a manic state was observed in the tail suspension test whereas both a manic state and a depressed state were observed in the forced swimming test. In addition, the fact that either a manic state or a depressed state was observed depending on the titer of the retrovirus vector used to introduce SITH-1 not only shows that the model of interest can serve as models of depression and manic-depressive illness alike but also suggests that the amount of expression of SITH-1 affects the symptoms of mental disorders.

Figure 10:
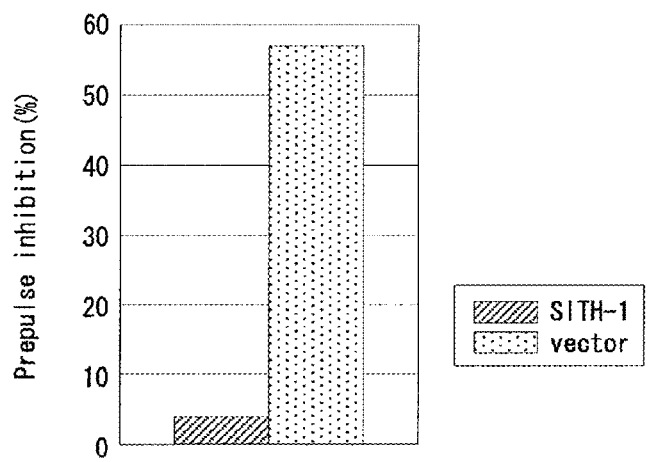
FIG. 10 is a graph showing the result of investigating the effect of SITH-1 in terms of prepulse inhibition.

The present inventors also measured the prepulse inhibition in order to check for any abnormality in the startle response that is to be found in patients with manic-depressive illness and schizophrenia. Specifically, the mice transfected with SITH-1 using the adenovirus vector were evaluated for a startle response by measuring the prepulse inhibition. The result is shown in FIG. 10; as it turned out, the SITH-1 transfected mice had a markedly lower prepulse inhibition, indicating that they had become overly sensitive to stimuli. Thus, considerable abnormality was also observed in the startle response, indicating that SITH-1 greatly affects the brain function associated with mental disorders.

5. Construction 2 of Model Mice with Mental Disorder by Expressing SITH-1

Next, the open reading frame of SITH-1 was linked downstream of the GFAP promoter and expressed in glial cells of mice using the adenovirus vector; three weeks later, the mice were measured for their motor activity in terms of wheel running activity. The result is shown in FIG. 11.

Figure 11:
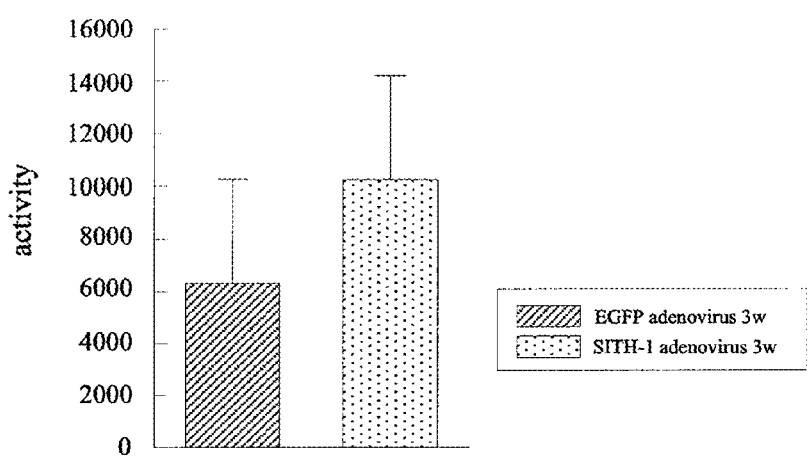
FIG. 11 is a graph showing the result of an experiment in which SITH-1 was expressed in mouse glial cells using an adenovirus vector and, 3 weeks later, the animals were measured for their motor activity in terms of wheel running activity.

As FIG. 11 shows, compared to the control mice in which EGFP (enhanced green fluorescence protein) was expressed, the SITH-1 expressing mice had their motor activity enhanced and they showed a tendency to be in a manic state.

6. Construction 3 of Model Mice with Mental Disorder by Expressing SITH-1

Subsequently, the open reading frame of SITH-1 was linked downstream of the GFAP promoter and expressed in glial cells of mice using the lentivirus vector; eight weeks later, the mice were measured for their motor activity in terms wheel running activity. The result is shown in FIG. 12.

Figure 12:
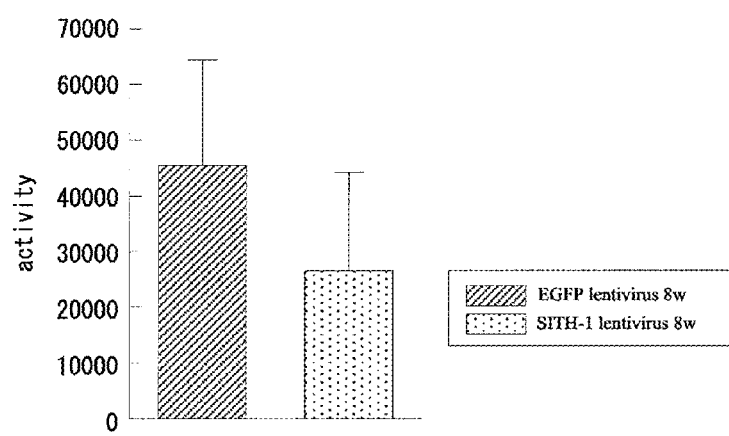
FIG. 12 is a graph showing the result of an experiment in which SITH-1 was expressed in mouse glial cells using a lentivirus vector and, 8 weeks later, the animals were measured for spontaneous motor activity under wheel running activity.

As FIG. 12 shows, compared to the control mice in which EGFP (enhanced green fluorescence protein) was expressed, the SITH-1 expressing mice had their motor activity suppressed and they showed a tendency to be in a depressed state.

As can be seen from FIGS. 11 and 12, the same SITH-1 was found to cause two opposite phenomena, a manic state and a depressed state. The reasons would be as follows: 1) SITH-1 carried by the adenovirus vector was expressed in a greater amount than when it was carried by the lentivirus vector; 2) on the other hand, the lentivirus vector allowed SITH-1 to be expressed for a longer period, so the effect of the prolonged expression of SITH-1 was observed.

This fact, i.e., model mice of a manic state and a depressed state can both be constructed by expressing SITH-1, may be described as providing a result in good agreement with the clinical finding that antibodies against SITH-1 are detected both from patients with manic-depressive illness and from patients with depression.

7. Diagnosis Using SITH-1 as a Marker

A study was made to see if diagnosis based on SITH-1 would also be useful in diagnosing other diseases associated with depression. The results are shown in FIG. 13.

Diagnosis based on the anti-SITH-1 antibody is quite specific to mood disorders such as depression, manic-depressive illness, and chronic fatigue syndrome. However, as FIG. 13 shows, the same diagnosis exceptionally showed high positive rate among patients with Crohn's disease. No positive outcome was shown by patients with ulcerative colitis which was similar to Crohn's disease.

Figure 13:
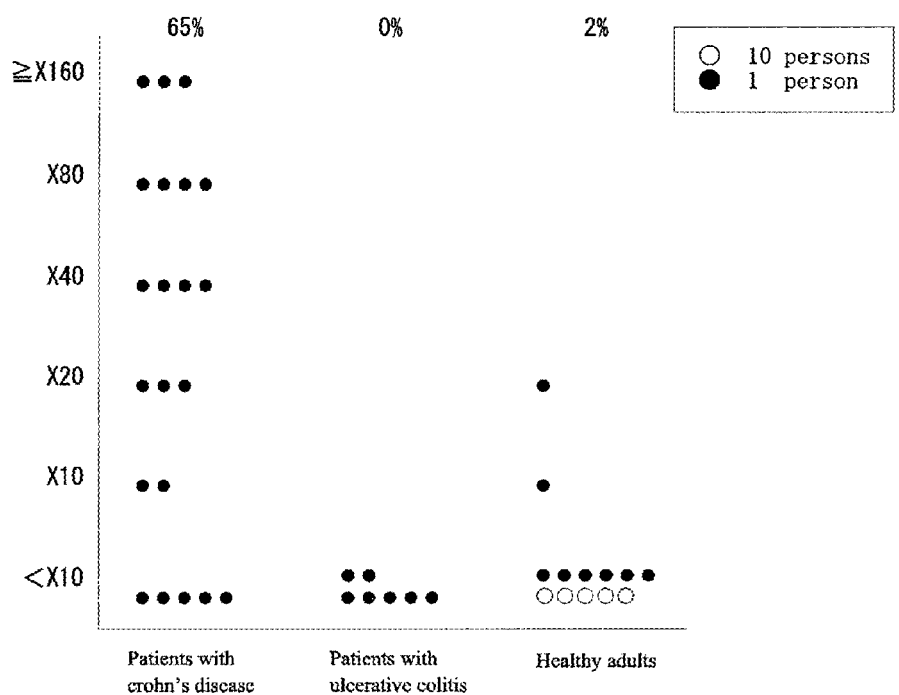
FIG. 13 is a graph showing the results of diagnosing, with SITH-1 used as an index, various diseases that will be complicated by depression.

However, it is known that Crohn's disease is most frequently complicated by "depressive symptoms" and the anti-SITH-1 antibody positive persons depicted in FIG. 13 are cases of Crohn's disease that were serious enough to be complicated by depressive symptoms. The example under consideration shows that even in such serious cases that patients with Crohn's disease which is a chronic disease classified as an autoimmune disease also present with depressive symptoms, depression can be diagnosed using SITH-1 as a marker. In other words, testing with the anti-SITH-1 antibody may be considered to be "also useful in diagnosis of depression that is caused by other, non-psychiatric diseases."

Example 1: Expression of SITH-1 in the Presence of Ganciclovir

The human glial cell line (U373) was infected with HHV-6 in the presence of ganciclovir, and the amount of SITH-1 expressed in the infected cell line was measured by the real-time PCR technique.

The U373 cells were cultured overnight in the presence of ganciclovir at various concentrations (FIG. 14) and infected with an HHV-6 variant B HST strain, and the amount of SITH-1 that was expressed in cells one day after the infection was measured by the real-time PCR technique.

Since the effective concentration of ganciclovir against HHV-6 variant B is considered to be about 10 μM in terms of $IC_{50}$, three concentrations were obtained by 3-fold dilutions, with 10 μM in the middle.

The primers and the TaqMan probe used had the following sequences:

PCR primer forward: 5'-CGTACCACTACTGATCTC-GAAGC-3' (SEQ ID NO:11)
PCR primer reverse: 5'-CTGTGGTCCAGGAACATG-TAATG-3' (SEQ ID NO:12)
TaqMan probe: 5'-CTTCTGTACATACCGATTCTGTGAC-GAGCC-3' (SEQ ID NO:13)

Figure 14:
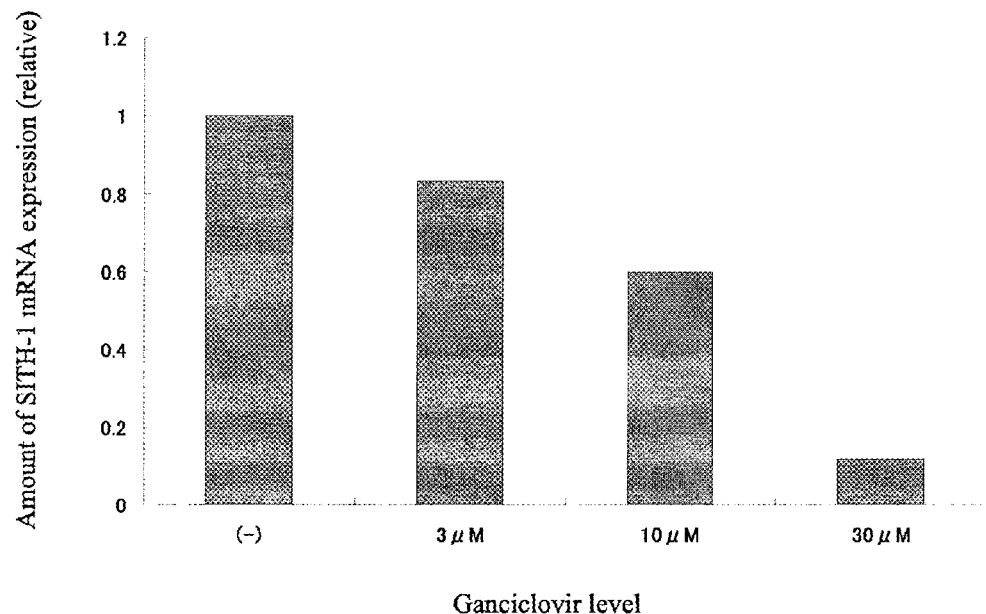
FIG. 14 is a graph showing the results of suppressing the expression of SITH-1 by ganciclovir.

The results are shown in FIG. 14. The vertical axis of the graph in FIG. 14 plots the relative amount of expression of SITH-1 mRNA, with the value for ganciclovir (-) being taken as unity. Ganciclovir was found to suppress the expression of SITH-1 in the glial cell line (U373) infected with HHV-6. When ganciclovir was used in the amounts of 3 M, 10 μM and 30 μM, the amount of expression of SITH-1 mRNA was suppressed by about 20%, 40% and more than 80%, respectively.

Example 2: Expression of CAML in the Presence of Ganciclovir

The human glial cell line (U373) is infected with HHV-6, and then ganciclovir is added. The amount of CAML expressed in the infected cell line in the presence of ganciclovir is measure by the indirect fluorescent antibody technique.

As a result, it is shown that the amount of CAML expression is suppressed by ganciclovir in a dose-dependent manner in the U373 cell line.

The invention claimed is:

1. A method of treating a subject with a mood-disorder or a subject susceptible to a mood disorder comprising:
   detecting whether the antibody titer against SITH-1 protein in a biological sample from the subject is significantly higher compared to the average anti-SITH-1 antibody titer of healthy subjects;
   diagnosing the subject to be with a mood disorder or susceptible to a mood disorder when a significantly higher antibody titer is detected; and
   administering to said diagnosed subject a therapeutically effective dose of at least one human herpesvirus 6 (HHV-6) suppressor.

2. The method of treating a subject with a mood disorder or a subject susceptible to a mood disorder according to claim 1,
   wherein said dose of said HHV-6 suppressor administered is sufficient to suppress an elevation of the level of SITH-1 protein within cells of said subject's brain, reduce the number of cells carrying SITH-1 protein within said subject's brain, and/or reduce the total amount of SITH-1 protein in said subject's brain.

3. The method of treating a subject with a mood disorder or a subject susceptible to a mood disorder according to claim 1,
   wherein said dose of said HHV-6 suppressor administered is sufficient to suppress an elevation of the level of a calcium modulating cyclophilin ligand (CAML) protein within cells of said subject's brain.

4. The method of treating a subject with a mood disorder or a subject susceptible to a mood disorder according to claim 1,
   wherein said dose of said HHV-6 suppressor administered is sufficient to suppress an elevation of the level of calcium ions within cells of said subject's brain.

5. The method according to any one of claims 1-4, wherein said HHV-6 suppressor is an anti-human herpesvirus 6 drug (anti-HHV-6 drug) or a HHV-6 reactivation suppressor.

6. The method of claim 5, wherein said anti-HHV-6 drug is selected from the group consisting of ganciclovir, valganciclovir, foscarnet, famciclovir, and idoxuridine (IDU).

7. The method of claim 5, wherein said virus reactivation suppressor is selected from the group consisting of D-ribose, vitamin C, and an active hexose correlated compound (AHCC).

8. The method according to any one of claims 2-4, wherein said cells in said subject's brain are glial cells.

9. The method according to any one of claims 1-4, wherein said biological sample is blood, serum, cerebrospinal fluid, saliva, sweat, lymph, or breast milk.

10. The method according to any one of claims 1-4, wherein SITH-1 protein is encoded by:
    (1) a nucleic acid coding for a protein comprising the amino acid sequence of SEQ ID NO: 1; or
    (2) a nucleic acid comprising the nucleotide sequence of SEQ ID NO: 2.

11. A method for treating or preventing a mood disorder comprising:
    detecting SITH-1 protein encoded by an intermediate stage transcript of HHV-6 and/or an antibody against SITH-1 protein in a biological sample taken from a subject,
    comparing the amount of SITH-1 encoded by an intermediate stage transcript of HHV-6 and/or the amount of an antibody against SITH-1 protein in said biological sample to the amount of SITH-1 protein encoded by an intermediate stage transcript of HHV-6 or an antibody against SITH-1 in a biological sample from a healthy subject;

diagnosing the subject with a mood disorder when the amount of SITH-1 protein encoded by the intermediate stage transcript of HHV-6 and/or the amount of the antibody against SITH-1 protein in said subject is two times or more than the corresponding amount in the healthy subject; and administering a human herpesvirus 6 suppressor to the diagnosed subject.

12. A method for treating or preventing a mood disorder comprising:

detecting whether the antibody titer against SITH-1 protein in a biological sample from a subject is significantly higher compared to the average anti-SITH-1 antibody titer of healthy subjects;

diagnosing the subject to be with a mood disorder or susceptible to a mood disorder when a significantly higher antibody titer is detected; and administering to the subject with a mood disorder or likely to suffer from mood disorder (a) a human herpesvirus 6 suppressor or (b) an agent that suppresses human herpesvirus 6 infection, proliferation, latent infection and/or reactivation.

13. The method of claim 1, wherein said HHV-6 suppressor is administered to said subject after said biological sample has been taken from said subject and said antibody against SITH-1 protein has been detected.

14. A method for treating a human subject diagnosed as having a mood disorder, comprising:

diagnosing whether the subject has a mood disorder by the steps of:

(i) determining in a sample obtained from the subject, the level of SITH-1 antibody, and (ii) determining whether or not the subject has a mood disorder based on the level of the antibody that recognizes said SITH-1 protein in the subject, wherein the subject whose biological sample shows a significantly higher antibody titer against SITH-1 protein compared to the average anti-SITH-1 antibody titer of healthy subjects is determined as having a mood disorder, and wherein the mood disorder is selected from the group consisting of depression and manic-depression illness; and administering to said subject a therapeutically effective dose of at least one human herpesvirus 6 (HHV-6) suppressor.

15. A method of treating a subject with a mood disorder or a subject susceptible to a mood disorder comprising:

diagnosing the subject to be with a mood disorder or susceptible to a mood disorder in the case that, in a biological sample from the subject, a significantly higher antibody titer against SITH-1 protein compared to the average anti-SITH-1 antibody titer of healthy subjects is detected; and administering to said diagnosed subject a therapeutically effective dose of at least one human herpesvirus 6 (HHV-6) suppressor.

* * * * *

SEQUENCE LISTING

<160> NUMBER OF SEQ ID NOS: 13

<210> SEQ ID NO 1
<211> LENGTH: 159
<212> TYPE: PRT
<213> ORGANISM: Human herpesvirus 6

<400> SEQUENCE: 1

Met Gly Tyr Glu Glu Lys Val Ser Ala Thr Gly Lys Thr Arg Leu Lys
1               5                   10                  15

Ile Leu Ala Cys Leu Ile Val Leu Ile Leu Ala Ala Ala Ile Thr Met
                20                  25                  30

Leu Thr Leu Glu Ile Ile Ser Asn Gln Lys Arg Thr Thr Thr Asp Leu
            35                  40                  45

Glu Ala Val Thr Val Ala Leu Lys His Val Ser Thr Ser Leu Ala Ser
        50                  55                  60

Cys Thr Glu Ser Thr Thr Ser Val His Thr Asp Ser Val Thr Ser Gln
65                  70                  75                  80

Pro Thr Lys Asn Lys Glu Ser Arg Lys Lys Ile Glu Gly Lys Ser Pro
                85                  90                  95

Ser Trp Val Gln Ala Leu Thr Thr Ala Ser Gly Ile Ile Leu Leu Phe
                100                 105                 110

Cys Ile Met Met Ile Phe Ile Thr Cys Ser Trp Thr Thr Glu Lys Asp
            115                 120                 125

Thr Glu Lys Ser Glu Val Gln Ser Tyr Ala Ser Ser Val Glu Thr Leu
        130                 135                 140

Asp Ser Leu Asn Glu Ala Ile Ile Pro Lys Thr Glu Met Asn Val
145                 150                 155

<210> SEQ ID NO 2
<211> LENGTH: 480
<212> TYPE: DNA
<213> ORGANISM: Human herpesvirus 6

<400> SEQUENCE: 2
atgggatatg aagaaaaagt gtcagctact ggaaagactc gtttaaagat actggcatgt      60
ctgatcgttt taatactagc tgcggcaata actatgttaa cgctggaaat tatatcgaac     120
caaaaacgta ccactactga tctcgaagct gtgactgtgg cgctgaagca tgtaagcaca     180
tctcttgcca gctgcactga atccactact tctgtacata ccgattctgt gacgagccaa     240
cccacgaaaa acaaagaatc gaggaaaaaa attgaaggga atctccaag ttgggttcag      300 gctttaacta cagcatctgg aattatccta ctgttttgta taatgatgat attcattaca     360

```
tgttcctgga ccacagaaaa agatacagag aagagtgaag tgcaatctta tgcttcttca      420
gtagagactt tagactcttt aaatgaggct attataccga aaactgaaat gaatgtgtaa      480
```

<210> SEQ ID NO 3
<211> LENGTH: 1795
<212> TYPE: DNA
<213> ORGANISM: Human herpesvirus 6

<400> SEQUENCE: 3

```
aggctctgct ggaggctctg ctggaggcct tgctgaaggc tctgctggag gccctgctgg       60
aggtcttgct ggaggctctg ctggaggctc tgctggaggc tctgctggag gctctgctgg      120
aggctctgct ggaggctctg ctggaggctc tgtcagagac ctcggtgaaa gttttactca      180
gaggtttatc agagttttcg ccattagttt ggttagaagt ttcagattta ttttcggtgg      240
aactgcagtt aggtttcatg tcagtacatt catcaccgtt agaagtgcta ttcatggtgc      300
tgttgccact gttggatttg ttaaaagcag taaatgagct aggattggaa tgactccgaa      360
tagctaataa atttgagcat tttcttcgaa tggatcataa tcagagggat agccatctaa      420
tttaaagact tccattttat cactgttgca atcacttcta atggagtatc tggatacatt      480
ttttctacat ctttttcatc ccctccaaca tggatctgtg cagcgttaat aagccagcgg      540
agttaattaa atcgtcttcc atgttagaca gttcctgttt catggcagcc ttcactgatg      600
caccaatact ttggatgcaa gtgccaacgg actgagctag gatgtaaaag aagatattct      660
aattttgaat tcttcagatg ctccttcttc cacattactg gaataggaca cattcttgga      720
agcgatgtcg ttggaagact ctgggatgaa agatcacag gcttccagtt ctggaaaaag      780
caggcttcca aggacacat cacacttgag actctcttcc aatatttctt tgatggattc      840
ttccaccact ggatcgggat ggtagctata tatactatat aaggagatta ccaccaccac      900
ctctttcttt gcagagatta ttctctgctt gaaaatctgt aacactgatc atgatgggat      960
atgaagaaaa agtgtcagct actggaaaga ctcgtttaaa gatactggca tgtctgatcg     1020
ttttaatact agctgcggca ataactatgt taacgctgga aattatatcg aaccaaaaac     1080
gtaccactac tgatctcgaa gctgtgactg tggcgctgaa gcatgtaagc acatctcttg     1140
ccagctgcac tgaatccact acttctgtac ataccgattc tgtgacgagc caacccacga     1200
aaaacaaaga atcgaggaaa aaattgaag ggaaatctcc aagttgggtt caggctttaa     1260
ctacagcatc tggaattatc ctactgtttt gtaatgat gatattcatt acatgtccct     1320
ggaccacaga aaagataca gagaagagtg aagtgcaatc ttatgctcct tcagtagaga     1380
ctttagaccc tttaaatgag gctattatac cgaaaactga atgaatgtg taatgtctgt     1440 attttttcttt acagagatgt acggagagtt tatatttggg gaaaataccct gactgttctg     1500 cctatatgcg aatgttaaag tatgtataat ataaattctt accttttaag agtgattcaa     1560
ggtggaggtt tctttggaga ttgattccag gtggtggttt cgggtgcaat caatctttct     1620
tctgggcggg aagaaaatcc agcaatccaa taattgatgg gatgtaatca atgtcacaaa     1680
tctgtaagat taaatgtgaa cagtataaat tctttcgtgc ttatcaaatt acaattatgc     1740
gcatgaaaat atcattaaat tgttttaaac attcttaaaa aaaaaaaaa aaaaa           1795
```

<210> SEQ ID NO 4
<211> LENGTH: 25
<212> TYPE: DNA
<213> ORGANISM: Artificial Sequence
<220> FEATURE:

```
<223> OTHER INFORMATION: Synthetic primer

<400> SEQUENCE: 4
gatgctcctt cttccacatt actgg                                              25

<210> SEQ ID NO 5
<211> LENGTH: 26
<212> TYPE: DNA
<213> ORGANISM: Artificial Sequence
<220> FEATURE:
<223> OTHER INFORMATION: Synthetic primer

<400> SEQUENCE: 5
catcccatca attattggat tgctgg                                             26

<210> SEQ ID NO 6
<211> LENGTH: 26
<212> TYPE: DNA
<213> ORGANISM: Artificial Sequence
<220> FEATURE:
<223> OTHER INFORMATION: Synthetic primer

<400> SEQUENCE: 6
gaaaccacca cctggaatca atctcc                                             26

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
gacacattct tggaagcgat gtcg                                               24

<210> SEQ ID NO 8
<211> LENGTH: 25
<212> TYPE: DNA
<213> ORGANISM: Artificial Sequence
<220> FEATURE:
<223> OTHER INFORMATION: Synthetic primer

<400> SEQUENCE: 8
gctgggtagt ccccaccttt ctaga                                              25

<210> SEQ ID NO 9
<211> LENGTH: 26
<212> TYPE: DNA
<213> ORGANISM: Artificial Sequence
<220> FEATURE:
<223> OTHER INFORMATION: Synthetic primer

<400> SEQUENCE: 9
ctgaagcatg taagcacatc tcttgc                                             26

<210> SEQ ID NO 10
<211> LENGTH: 23
<212> TYPE: DNA
<213> ORGANISM: Artificial Sequence
<220> FEATURE:
<223> OTHER INFORMATION: Synthetic primer

<400> SEQUENCE: 10
gcttcgagat cagtagtggt acg                                                23
```

```
<210> SEQ ID NO 11
<211> LENGTH: 23
<212> TYPE: DNA
<213> ORGANISM: Artificial Sequence
<220> FEATURE:
<223> OTHER INFORMATION: Synthetic primer

<400> SEQUENCE: 11
cgtaccacta ctgatctcga agc                                              23

<210> SEQ ID NO 12
<211> LENGTH: 23
<212> TYPE: DNA
<213> ORGANISM: Artificial Sequence
<220> FEATURE:
<223> OTHER INFORMATION: Synthetic primer

<400> SEQUENCE: 12
ctgtggtcca ggaacatgta atg                                              23

<210> SEQ ID NO 13
<211> LENGTH: 30
<212> TYPE: DNA
<213> ORGANISM: Artificial Sequence
<220> FEATURE:
<223> OTHER INFORMATION: Synthetic primer

<400> SEQUENCE: 13
cttctgtaca taccgattct gtgacgagcc                                       30
```